United States Patent
Hanada et al.

(10) Patent No.: US 11,065,135 B2
(45) Date of Patent: Jul. 20, 2021

(54) THIN, NARROW TUBE AND DRAWING APPARATUS AND DRAWING METHOD FOR MANUFACTURING THE SAME

(71) Applicant: National Institute of Advanced Industrial Science and Technology, Tokyo (JP)

(72) Inventors: Kotaro Hanada, Tsukuba (JP); Kunio Matsuzaki, Tsukuba (JP)

(73) Assignee: NATIONAL INSTITUTE OF ADVANCED INDUSTRIAL SCIENCE AND TECHNOLOGY

( * ) Notice: Subject to any disclaimer, the term of this patent is extended or adjusted under 35 U.S.C. 154(b) by 0 days.

(21) Appl. No.: 16/358,232

(22) Filed: Mar. 19, 2019

(65) Prior Publication Data

US 2019/0274851 A1    Sep. 12, 2019

Related U.S. Application Data

(62) Division of application No. 14/417,852, filed as application No. PCT/JP2013/071027 on Aug. 2, 2013, now Pat. No. 10,271,971.

(30) Foreign Application Priority Data

Aug. 3, 2012  (JP) .............................. JP2012-173202
Jul. 30, 2013  (JP) .............................. JP2013-157819

(51) Int. Cl.
*B21C 1/24*  (2006.01)
*A61F 2/82*  (2013.01)
(Continued)

(52) U.S. Cl.
CPC .............. *A61F 2/82* (2013.01); *A61L 31/022* (2013.01); *B21B 17/04* (2013.01); *B21C 1/24* (2013.01);
(Continued)

(58) Field of Classification Search
CPC .... B21C 1/16; B21C 1/18; B21C 1/22; B21C 1/24; B21C 1/26; B21C 3/12; B21B 17/04
See application file for complete search history.

(56) References Cited

U.S. PATENT DOCUMENTS 2,091,001 A  *  8/1937  Kobberup ................. B21C 1/24
                                                     72/283
3,453,854 A  *  7/1969  Lombardo ................ B21C 1/26
                                                     72/284
(Continued)

FOREIGN PATENT DOCUMENTS

CN       101134231 A      3/2008
CN       101297777 A     11/2008
(Continued)

OTHER PUBLICATIONS

Werkhoven, R. J., W. H. Sillekens, and J. B. J. M. Van Lieshout. "Processing aspects of magnesium alloy stent tube." In Magnesium Technology 2011, pp. 419-424. Springer International Publishing, 2011. (Year: 2011).

(Continued)

*Primary Examiner* — Debra M Sullivan
(74) *Attorney, Agent, or Firm* — Ostrolenk Faber LLP

(57) ABSTRACT

Provided is a thin, narrow tube for use in a biodegradable medical device formed from a round tube made of a magnesium material as the base material, in which a desired outer diameter and an inner diameter are provided with good precision over the entire region in a longitudinal direction and a circumferential direction, and the length of biodegradation time can be controlled without changing a material composition. The thin, narrow tube is a thin, narrow tube of a biodegradable medical device, in which the thin, narrow tube is a round tube made of crystals containing magnesium (Mg) having a hexagonal crystal structure, and when the (Continued)

crystals forming the round tube are viewed in a round tube axis direction of the round tube, a hexagonal basal plane (0001) is oriented at a predetermined inclination angle with respect to a circumferential direction perpendicular to a radial direction (a direction from an inner surface to an outer surface) of the round tube.

11 Claims, 20 Drawing Sheets

(51) Int. Cl.
　　　A61L 31/02　　　(2006.01)
　　　B21B 17/04　　　(2006.01)
　　　A61L 31/14　　　(2006.01)
　　　C21D 7/00　　　(2006.01)
　　　C21D 9/08　　　(2006.01)
　　　C22F 1/06　　　(2006.01)
　　　C22C 1/02　　　(2006.01)

(52) U.S. Cl.
　　　CPC ....... A61F 2210/0004 (2013.01); A61L 31/14 (2013.01); A61L 31/148 (2013.01); C21D 7/00 (2013.01); C21D 9/08 (2013.01); C21D 2201/05 (2013.01); C22C 1/02 (2013.01); C22F 1/06 (2013.01)

(56) References Cited

U.S. PATENT DOCUMENTS 3,474,652 A * 10/1969 Marcovitch .............. B21C 1/26
　　　　　　　　　　　　　　　　　　　　72/190
3,709,020 A * 1/1973 Evans ...................... B21C 1/24
　　　　　　　　　　　　　　　　　　　　72/283

FOREIGN PATENT DOCUMENTS

| JP | 53-053559 A | 5/1978 |
| JP | A-07-051733 | 2/1995 |
| JP | A-2004-232077 | 8/2004 |
| JP | 2006-167078 A | 6/2006 |
| JP | A-2008-036076 | 2/2008 |
| JP | A-2008-106337 | 5/2008 |
| JP | A-2011-167752 | 9/2011 |
| WO | WO 2009/079282 A1 | 6/2009 |
| WO | WO 2010/118193 A2 | 10/2010 |
| WO | WO 2011/163236 A2 | 12/2011 |
| WO | WO 2011/163236 A9 | 12/2011 |

OTHER PUBLICATIONS

International Search Report dated Oct. 22, 2013 in corresponding International Application No. PCT/JP2013/071027 (2 pages).
Kazuhiro Nomura, "DES That Melt Away Will Appear Soon" in Nikkei Medical Online, Feb. 25, 2011, [retrieved on Jul. 1, 2013], Internet<URL:http://medical.nikkeibp.co.jp/leaf/mem/pub/report/t127/201102/518615.html&pr=1> (7 pages) (with partial English language translation).
T. Kokubo et al., "How Useful is SBF in predicting in vivo bone bioactivity?," Biomaterials 27 (2006), pp. 2907-2915.
Supplementary European Search Report dated Feb. 23, 2016 in corresponding European Patent Application No. 13825947.8 (4 pages).
Chinese Office Action, dated Oct. 28, 2015, issued in corresponding Chinese Patent Application No. 201380040292.5. Includes partial English translation of Search Report. Total 7 pages.
Kazunari Yoshida, et al., "Cold Drawing of Magnesium Alloy Tubes for Medical," Journal of Solid Mechanics and Materials Engineering, Japan, vol. 5, No. 12 (2011), pp. 1071-1078.

* cited by examiner

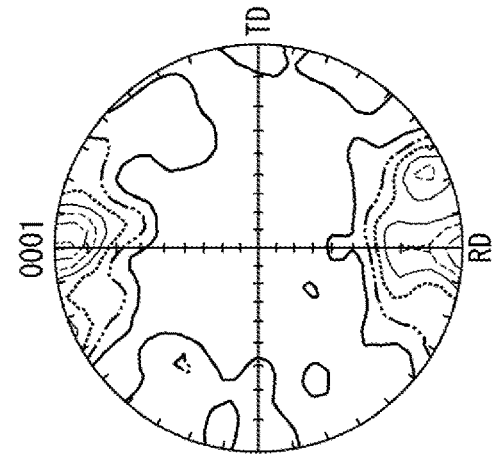
FIG. 15A EXTRUDED MATERIAL (φ2mm)
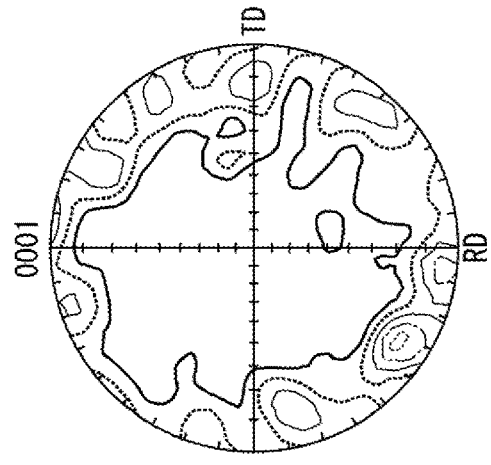
FIG. 15B DRAWN TUBE (φ1.9mm)
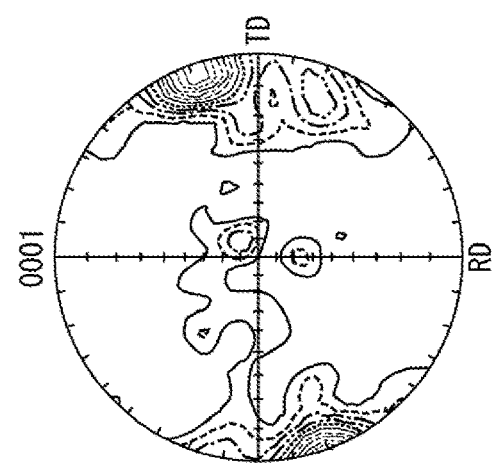
FIG. 15C DRAWN TUBE (φ1.5mm)
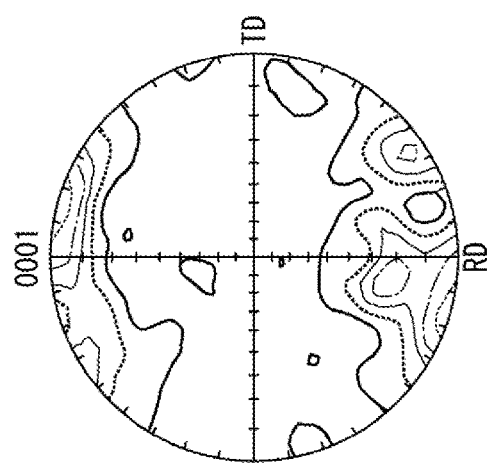
FIG. 15D METAL CORE DRAWN TUBE (φ1.8mm)

EXTRUDED MATERIAL (φ2mm)

DRAWN TUBE (φ1.9mm)

DRAWN TUBE (φ1.5mm)

METAL CORE DRAWN TUBE (φ1.8mm)

FIXED MANDREL DRAWING

ROTATING FIXED-MANDREL DRAWING

INCLINATION OF ABOUT 5° WITH RESPECT TO INNER SURFACE AND LONGITUDINAL DIRECTION

ROTATING METAL CORE DRAWING

INCLINATION OF 5° TO 10° WITH RESPECT TO INNER SURFACE AND LONGITUDINAL DIRECTION

METAL CORE DRAWING

THIN, NARROW TUBE AND DRAWING APPARATUS AND DRAWING METHOD FOR MANUFACTURING THE SAME

CROSS-REFERENCE TO RELATED APPLICATIONS

The present application is a divisional of prior U.S. patent application Ser. No. 14/417,852, filed Jan. 28, 2015, by Kotaro HANADA and Kunio MATSUZAKI, entitled "THIN, NARROW TUBE AND DRAWING APPARATUS AND DRAWING METHOD FOR MANUFACTURING THE SAME," which is a 35 U.S.C. §§ 371 national phase conversion of PCT/JP2013/071027, filed Aug. 2, 2013, which claims priority to Japanese Patent Application No. 2012-173202, filed Aug. 3, 2012, and Japanese Patent Application No. 2013-157819, filed Jul. 30, 2013. The PCT International Application was published in the Japanese language. The entire contents of each of these patent applications are incorporated herein by reference.

TECHNICAL FIELD

The present invention relates to a thin, narrow tube, and a drawing apparatus and a drawing method for manufacturing the same. More specifically, the present invention relates to a thin, narrow tube which is appropriate for use in a biodegradable medical device represented by a stent, and a drawing apparatus and a drawing method for manufacturing the same.

BACKGROUND ART

As an effective treatment method for coronary artery disease such as angina pectoris or myocardial infarction, there is a percutaneous coronary intervention (PCI). This is a treatment method performed using a catheter, and has become the mainstream of a coronary artery disease treatment after the 1990s due to an extremely low burden on a patient compared to that of other surgical procedures.

In the PCI, a mesh-like metallic tube called a stent, which is manufactured by performing laser processing on a thin, narrow tube, is very effective in securing blood flow in a narrowed or infarcted blood vessel, and is currently an essential device (PTL 1). A stent which is widely used in the PCI is made of SUS316L which is a material mainly used for medical purposes, tantalum, a cobalt alloy, nickel, a titanium alloy, or the like. However, since the stent is semipermanently placed in a treated vascular disease site, there is a problem of recurrence of stenosis and the like.

In order to solve this problem, "a stent decomposable and dissolvable in the body" is intensively examined, and for example, a stent base material made of a biodegradable polymer has been developed (NPL 1). However, as described in NPL 1, the biodegradable polymer has a weak "force to support a blood vessel", and thus is insufficient to secure blood flow in a narrowed site. Therefore, a stent made of metal is more expected in terms of force to support a blood vessel than that made of polymer. Particularly, magnesium is originally present as a body element and has excellent biodegradability, and thus is a promising stent base material. In the present invention, a medical device represented by a stent base material having excellent biodegradability is called a biodegradable medical device.

Recently, a stent (mesh-like metallic tube) which employs a magnesium material as a base material has received attention all over the world as a next-generation minimally-invasive stent in which a burden on a patient is much smaller than that of an existing stent.

However, it is difficult to control time (biodegradation time) for the magnesium material to disappear in vivo compared to that of a polymer. In addition, the magnesium material has a hexagonal close-packed (hcp) structure, and thus a slip system during deformation at room temperature is limited only to (0001). Therefore, ductility is insufficient and breaking easily occurs in a stage of expanding a stent. In order to control the length of the biodegradation time and enhance ductility, a method of changing a material composition is well-known. However, a method of changing a material composition one by one has poor mass production efficiency.

In addition, since the magnesium material has a lower tensile strength than an iron-based material or an aluminum-based material and has a hexagonal close-packed (hcp) structure, a slip system during deformation at room temperature is limited only to (0001), and the workability is extremely insufficient.

Therefore, in the related art, it is difficult to obtain a long, thin, and narrow magnesium tube (round tube) having a diameter of 2 [mm] or less, a thickness of 200 [μm] or less, a length of 500 [mm] or greater, and a dimensional precision of 0.15 [%] or less, which is necessary to process a stent. The magnesium round tube is produced by cutting or drawing a cast material or a material obtained by forging or extruding the cast material. However, the dimensional precision is poor, and the obtained length also does not satisfy 100 [mm].

As existing methods of processing a round tube, there are an extrusion method of extruding a billet into a hollow tube by using a mandrel, a seam welding method of performing cold winding on a plate into a cylindrical shape and welding butting portions, a drawing method (PTLs 2 and 3) of drawing a raw tube by using a die or a roll and reducing the cross-sectional area of the raw tube, and a deposition method or a sputter deposition method of directly coating a metal core with a round tube (PTL 4). However, the extrusion method and the seam welding method are limited to a case of manufacturing a round tube having a relatively large tube diameter from the viewpoint of process limitations, or the dimensions of a processing object, die strength, and the like, and thus cannot be applied to a case of manufacturing a thin, narrow tube. In a case of manufacturing a thin, narrow tube, the deposition method, the sputter deposition method, and the drawing method (PTL 3) are mainly used.

According to the deposition method and the sputter deposition method, an extremely thin, narrow tube having a tube diameter of 1 [mm] or less and a thickness of several tens of [μm] can be manufactured. However, it is difficult to process a long round tube due to limitations on the dimensions of the chamber and the metal core.

Hereinafter, a method of manufacturing a thin, narrow tube by using the drawing method will be described in more detail. In addition, the thin, narrow tube manufactured by using the drawing method is also called a drawn body.

The drawing method will be described with reference to FIGS. 13A-13D. The drawing method is broadly classified into four methods which are tube sinking, fixed plug drawing, floating plug drawing, and mandrel drawing. As shown in FIG. 13A, the tube sinking is a method of drawing only a round tube 213 using a die 211. A roll may also be used instead of the die 211. During the tube sinking, as the process progresses, wrinkles are generated in an inner wall surface 213a of the round tube 213 and thus the thickness locally varies. Therefore, there is a problem in that the inner wall surface 213a cannot obtain dimensional precision.

As shown in FIG. 13B, the fixed plug drawing is a method of allowing a plug 222B fixed to a support bar 222A to pass through an inside 223c of a round tube 223 and drawing the round tube by using the die 211 while supporting an inner wall surface 223a of the round tube with the plug 222B. A roll may also be used instead of the die 221. According to the fixed plug drawing, both the inner wall surface 223a and an outer wall surface 223b can obtain high dimensional precision. However, in a case where the round tube 223 to be processed is a narrow tube or a long tube, there is a problem in that it is technically difficult to manufacture the plug support bar 222A having a strength applicable to the case.

As shown in FIG. 13C, the floating plug drawing is a method of allowing a plug 232 which is not fixed to pass through an inside 233c of a round tube 233 and drawing the round tube by using a die 231 while supporting an inner wall surface 233a of the round tube 233 with the plug 232. A roll may also be used instead of the die 231. Since a support bar that fixes the plug 232 thereto is not used, the method can be applied to a case where the round tube 233 to be processed is a narrow tube or a long tube. However, since the direction of the plug 232 is easily changed and the inner wall surface 233a of the round tube cannot be supported with a uniform force, the dimensional precision of the inner wall surface 233a is inferior to that of the fixed plug drawing. In addition, the processing force during the floating plug drawing is strong, and thus the round tube 233 may receive an excessive pressure during the processing and may be easily broken. In addition, in a case where the inner diameter of the round tube 233 is 1 [mm] or less, it is technically difficult to manufacture the plug 232 having a shape applicable to the case. Even when the plug can be manufactured, there is a problem in that handling is difficult.

As shown in FIG. 13D, the mandrel drawing is a method of drawing a round tube 243 in a state where a mandrel 242 is inserted therethrough by using a die 241. A roll may also be used instead of the die 241. The mandrel drawing is a method applicable even when the round tube 243 is a narrow tube or a long tube. However, after the drawing, the mandrel 242 needs to be drawn out from the round tube 243. However, in a case where the round tube 243 is made of a material having a low strength, such as a magnesium material, when the mandrel 242 is drawn out, the entire round tube 243 may be deformed, and both an inner wall surface 243a and an outer wall surface 243b cannot obtain high dimensional precision. As a result, it is difficult to process the round tube 243 after the mandrel drawing into a desired mesh-like shape using a laser or the like in order to form a stent.

CITATION LIST

Patent Literature

[PTL 1] Japanese Unexamined Patent Application, First Publication No. 2008-36076
[PTL 2] Japanese Unexamined Patent Application, First Publication No. H07-51733
[PTL 3] Japanese Unexamined Patent Application, First Publication No. 2011-167752
[PTL 4] Japanese Unexamined Patent Application, First Publication No. 2004-232077

Non-Patent Literature

[NPL 1] "DES That Melt Away Will Appear Soon" in Nikkei Medical Online, by Kazuhiro Nomura, Feb. 25, 2011.

SUMMARY OF INVENTION

Technical Problem

The present invention has been made taking the foregoing circumstances into consideration, and a first object thereof is to provide a thin, narrow tube which is a thin, narrow tube for use in a biodegradable medical device formed from a round tube made of a magnesium material as the base material, in which a desired outer diameter and an inner diameter are provided with good precision over the entire region in the longitudinal direction and the circumferential direction, and a deformation ratio can be improved and the length of biodegradation time can be controlled without changing a material composition.

In addition, a second object of the present invention is to provide a drawing apparatus and a drawing method for manufacturing a thin, narrow tube, capable of reducing the diameter of a round tube having a final thickness to achieve desired inner diameter and outer diameter with good precision over the entire region in the longitudinal direction and the circumferential direction.

Solution to Problem

A thin, narrow tube according to the present invention is a thin, narrow tube of a biodegradable medical device, in which the thin, narrow tube is a round tube made of crystals containing magnesium (Mg) having a hexagonal crystal structure, and when the crystals forming the round tube are viewed in a round tube axis direction of the round tube, a hexagonal basal plane (0001) is oriented at a predetermined inclination angle with respect to a circumferential direction perpendicular to a radial direction (a direction from an inner surface to an outer surface) of the round tube.

In the thin, narrow tube of the present invention as described above, the orientation is specified in a pole figure obtained by using an electron back-scatter diffraction (EBSD) method performed on a radial cross-section (a surface perpendicular to a round tube axis) of the round tube, and a strong signal caused by a high-density orientation structure A having a peak intensity of $6/7$ or more of a maximum peak intensity in the hexagonal basal plane (0001) is observed within an inclination angle of ±30° with respect to the circumferential direction, and the high-density orientation structure A is oriented.

In the thin, narrow tube according to the present invention as described above, angle zones in which a weak signal caused by a low-density orientation structure B having a peak intensity of $1/7$ of the maximum peak intensity in the hexagonal basal plane (0001) is observed are discretely provided.

In the thin, narrow tube according to the present invention as described above, the high-density orientation structure A is further oriented in a spiral shape in a longitudinal direction of the round tube.

A drawing apparatus according to the present invention is a drawing apparatus for manufacturing the thin, narrow tube as described above, including at least: first means including a part α which surrounds a round tube while being in contact with the round tube in a circumferential direction to reduce a diameter of the round tube; and cylindrical second means which is disposed to oppose a minimum inner diameter portion of the part α and of which a side surface supports the round tube, in which a center axis of the minimum inner diameter portion and a center axis of the second means coincide with a drawing direction of the round tube, the first means and the second means are separated from each other over entire circumferences by a thickness of the round tube, and means for allowing one end of the second means to protrude from the minimum inner diameter portion in the drawing direction of the round tube and to retreat with respect to movement of the round tube is included.

In the drawing apparatus of the present invention as described above, the part α of the first means includes means for coming into contact with an outer surface of the round tube which advances in the drawing direction and rotating along the outer surface of the round tube.

A drawing apparatus according to the present invention is a drawing apparatus for manufacturing the thin, narrow tube as described above, the apparatus including at least: first means including a part α which surrounds a round tube while being in contact with the round tube in a circumferential direction to reduce a diameter of the round tube; and cylindrical second means which is disposed to oppose a minimum inner diameter portion of the part α and of which a side surface supports the round tube, in which a center axis of the minimum inner diameter portion and a center axis of the second means coincide with a drawing direction of the round tube, the first means and the second means are separated from each other over entire circumferences by a final thickness of the round tube, and the part α of the first means includes means for coming into contact with an outer surface of the round tube which advances in the drawing direction and rotating along the outer surface of the round tube when the second means is allowed to advance in the drawing direction of the round tube according to movement of the round tube while one end of the second means is allowed to protrude from the minimum inner diameter portion in the drawing direction of the round tube.

In the drawing apparatus according to the present invention as described above, one end of the second means protrudes outward from a space surrounded by the first means.

In the drawing apparatus according to the present invention as described above, the first means is a die.

In the drawing apparatus according to the present invention as described above, the first means is a roll.

In the drawing apparatus according to the present invention as described above, the second means is a mandrel.

A drawing method according to the present invention is a drawing method of manufacturing a thin, narrow tube as described above by using the drawing apparatus as also described above, the method including: a process A of inserting the round tube which is supported by the second means from inside into the part α, and drawing only the round tube from the part α while reducing the diameter of the round tube to maintain the thickness of the round tube.

In the drawing method according to the present invention as described above, a process B of performing a heating treatment on the round tube subjected to the process A is further included.

In the drawing method according to the present invention as described above, the process A and process B are sequentially repeated.

In the drawing method according to the present invention as described above, in the process A, a drawing rate is adjusted so that a maximum reduction in an area of a cross-section of the round tube, which is perpendicular to the longitudinal direction, is 14.3[%] or higher and 15.4[%] or less.

A drawing method according to the present invention is a drawing method for manufacturing a thin, narrow tube as described above by using the drawing apparatus as described above, including: a process X of inserting the round tube which is supported by the second means from inside into the part α and drawing the round tube along with the second means from the part α to reduce the diameter of the round tube while reducing the thickness of the round tube.

In the drawing method according to the present invention as described above, a process Y of performing a heating treatment on the round tube subjected to the process X is further included.

In the drawing method according to the present invention as described above, the process X and process Y are sequentially repeated.

Advantageous Effects of Invention

Even though the thin, narrow tube according to the present invention is formed from the round tube made of a hardly processible magnesium material as the base material, a desired outer diameter, an inner diameter, and a thickness can be provided with good precision over the entire region in the circumferential direction and longitudinal direction. In addition, without changing the material composition of the base material, a deformation ratio can be improved and the length of biodegradation time can be controlled. Therefore, the present invention contributes to providing a thin, narrow tube for a biodegradable medical device.

In addition, in the thin, narrow tube according to the present invention, with the configuration in which the strong signal caused by the high-density orientation structure A having a peak intensity of $6/7$ or more of the maximum peak intensity in the hexagonal basal plane (0001) is observed within a range of ±30° with respect to the circumferential direction, a round tube having a higher thickness deformation ratio or a width direction deformation ratio than that in the related art (metal core drawing) can be obtained.

Furthermore, in the thin, narrow tube according to the present invention, with the configuration in which an angle range in which the weak signal caused by the low-density orientation structure B having a peak intensity of $1/7$ of the maximum peak intensity in the hexagonal basal plane (0001) is observed is provided, a round tube having a higher corrosion speed or a corrosion rate than that in the related art (metal core drawing) by 50% or more can be obtained.

Particularly, in the thin, narrow tube according to the present invention, with the configuration in which the high-density orientation structure A is further oriented in a spiral shape in the longitudinal direction of the round tube which is the drawn body, a round tube in which two factors, the thickness reduction and the width reduction, are most balanced can be obtained.

In the drawing apparatus according to the present invention, the center axis of the part of the first means and the center axis of the second means during the drawing of the round tube are configured to coincide with the drawing direction of the round tube. In addition, during the drawing, over the entire region in the longitudinal direction and the circumferential direction, the round tube is configured so that the distance between the part of the first means and the side surface of the second means can be maintained to be constant.

With this configuration, in the drawing procedure, the entire outer wall surface of the round tube and the entire inner wall surface of the round tube are respectively pressed against the part of the first means and the side surface of the second means with equal forces. In addition, by adjusting the drawing rate of the round tube, the round tube can be processed to have desired outer and inner diameters with good precision over the entire region in the longitudinal and circumferential directions.

Furthermore, according to the configuration of the drawing apparatus of the present invention, since the first means and the second means are separated from each other by the final thickness of the round tube, that is, separated by a distance, in the part which reduces the diameter of the round tube during the drawing of the round tube, the thickness of the round tube does not become smaller than that before the processing by the drawing. Therefore, the thickness of the round tube can be maintained before and after the drawing, and thus the deformation of the round tube due to a reduction in thickness as in the related art can be avoided. Accordingly, the round tube can be controlled to have desired outer and inner diameters with good precision over the entire region in the longitudinal and circumferential directions.

Moreover, according to the configuration of the drawing apparatus of the present invention, since the means for allowing one end of the second means to protrude from the part of the first means in the drawing direction of the round tube and to retreat with respect to movement of the round tube is included, only the round tube can be drawn by being separated from the second means. Therefore, the deformation of the wall portion of the round tube by further drawing out the second means from the round tube after the drawing using the first means as in the mandrel drawing of the related art can be avoided.

Furthermore, in the drawing apparatus of the present invention, since the part α of the first means includes the means for coming into contact with the outer surface of the round tube which advances in the drawing direction and rotating along the outer surface of the round tube, the thickness deformation ratio and the width direction deformation ratio of the round tube can be suppressed, and the grain sizes of the crystal grains included in the round tube can be increased. As a result, according to the drawing apparatus of the present invention, a round tube having a smaller corrosion speed or a corrosion rate than that in a case where the rotating means is not provided by about 30% can be manufactured.

In addition, in the drawing apparatus of the present invention, since the part α of the first means includes the means for coming into contact with the outer surface of the round tube which advances in the drawing direction and rotating along the outer surface of the round tube when second means is also allowed to advance in the drawing direction of the round tube according to movement of the round tube, the thickness deformation ratio and the width direction deformation ratio of the round tube can be suppressed, and the grain sizes of the crystal grains included in the round tube can be increased. As a result, according to the drawing apparatus of the present invention, a round tube having a smaller corrosion speed or a corrosion rate than that in a case where the rotating means is not provided by about 30% can be manufactured.

BRIEF DESCRIPTION OF DRAWINGS

FIG. 15A is a graph showing the result of Sample 1 of Experimental Example 5.

FIG. 15B is a graph showing the result of Sample 2 of Experimental Example 5.

FIG. 15C is a graph showing the result of Sample 3 of Experimental Example 5.

FIG. 15D is a graph showing the result of Sample 4 of Experimental Example 5.

DESCRIPTION OF EMBODIMENTS

Figure 1:
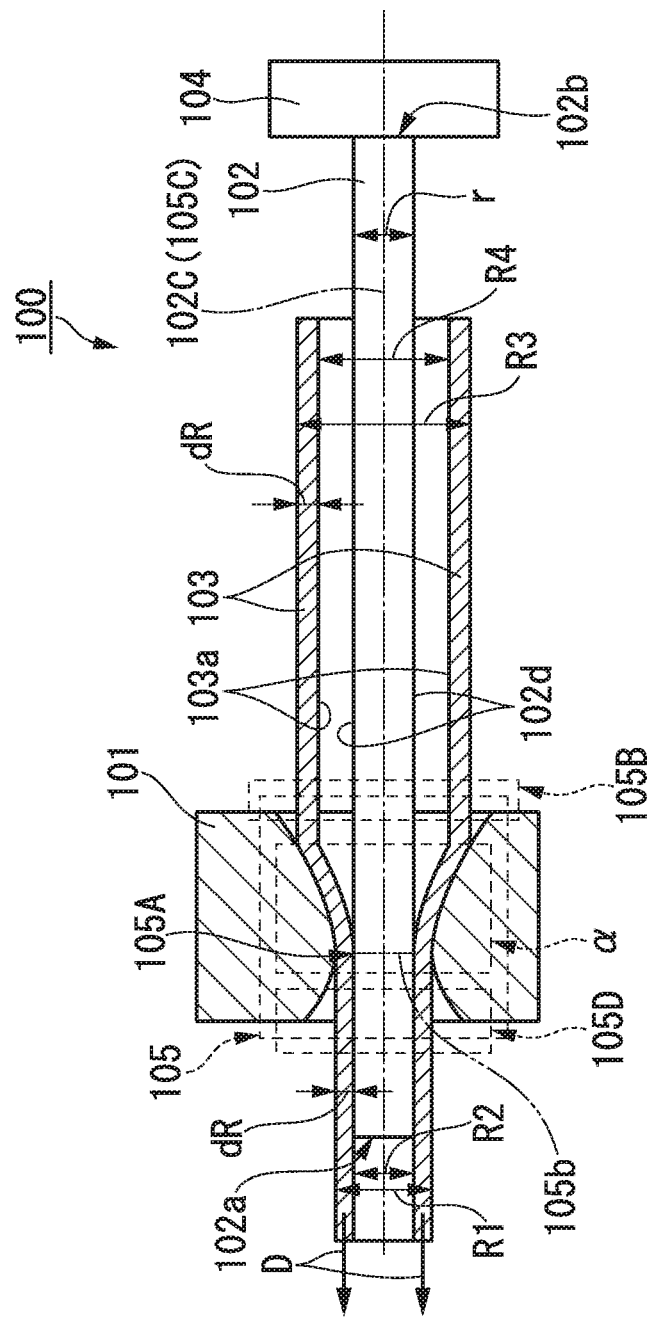
FIG. 1 is a view schematically showing the configuration of a drawing apparatus according to a first embodiment of the present invention.

Hereinafter, the present invention will be described on the basis of preferred embodiments with reference to the drawings. In addition, the following embodiments are exemplified to facilitate understanding of the concept of the present invention and do not limit the present invention if not particularly designated. In the drawings used for the description, for convenience, there may be cases where main parts are enlarged to facilitate understanding of the features of the present invention, and dimensional ratios of the elements are not limited to those in practice. Furthermore, round tubes in the present invention are not limited to truly round tubes.

First Embodiment

[Drawing Apparatus]

The configuration of a drawing apparatus of the present invention will be described. The drawing apparatus of the present invention includes at least first means, second means, and a fixing tool of the second means. The first means includes a part α which surrounds a round tube while being in contact therewith in a circumferential direction to reduce the diameter thereof. The second means has a cylindrical shape and is disposed to oppose a minimum inner diameter portion of the part α of the first means so that the side surface thereof supports the inner wall surface of the round tube.

In the above-described configuration of the drawing apparatus, an example of a case in which a die is used as the first means 101 and a mandrel is used as the second means 102 will be described with reference to FIG. 1. FIG. 1 is a cross-sectional view of a drawing apparatus 100 taken along a plane parallel to a drawing direction D of the round tube 103 to be processed. The drawing apparatus 100 includes the die 101, the mandrel 102, and a fixing tool 104 of the mandrel.

The die (first means) 101 has a space (hereinafter, referred to as a through-hole) 105 which communicates with the external space, and in this space, the part α which surrounds the round tube while being in contact therewith in the circumferential direction to reduce the diameter thereof is provided. The cross-section of the minimum inner diameter portion 105A of the part α has a circular shape, and the inner diameter of the through-hole 105 in the minimum inner diameter portion 105A is substantially equal to a final outer diameter R1 of the round tube.

The inner diameter of the through-hole 105 in an opening 105B on the inlet side of the round tube 103 is preferably larger than an outer diameter R3 of the round tube before being processed, and more preferably, is gradually reduced toward the minimum inner diameter portion 105A from the opening 105B. In addition, the inner diameter of the through-hole 105 in an opening 105D on the outlet side of the round tube 103 may be equal to or larger than the final outer diameter R1 of the round tube. In addition, in FIG. 1, the example in which the die is used as the first means 101 is shown. However, a roll may also be used instead of the die.

Figure 14:
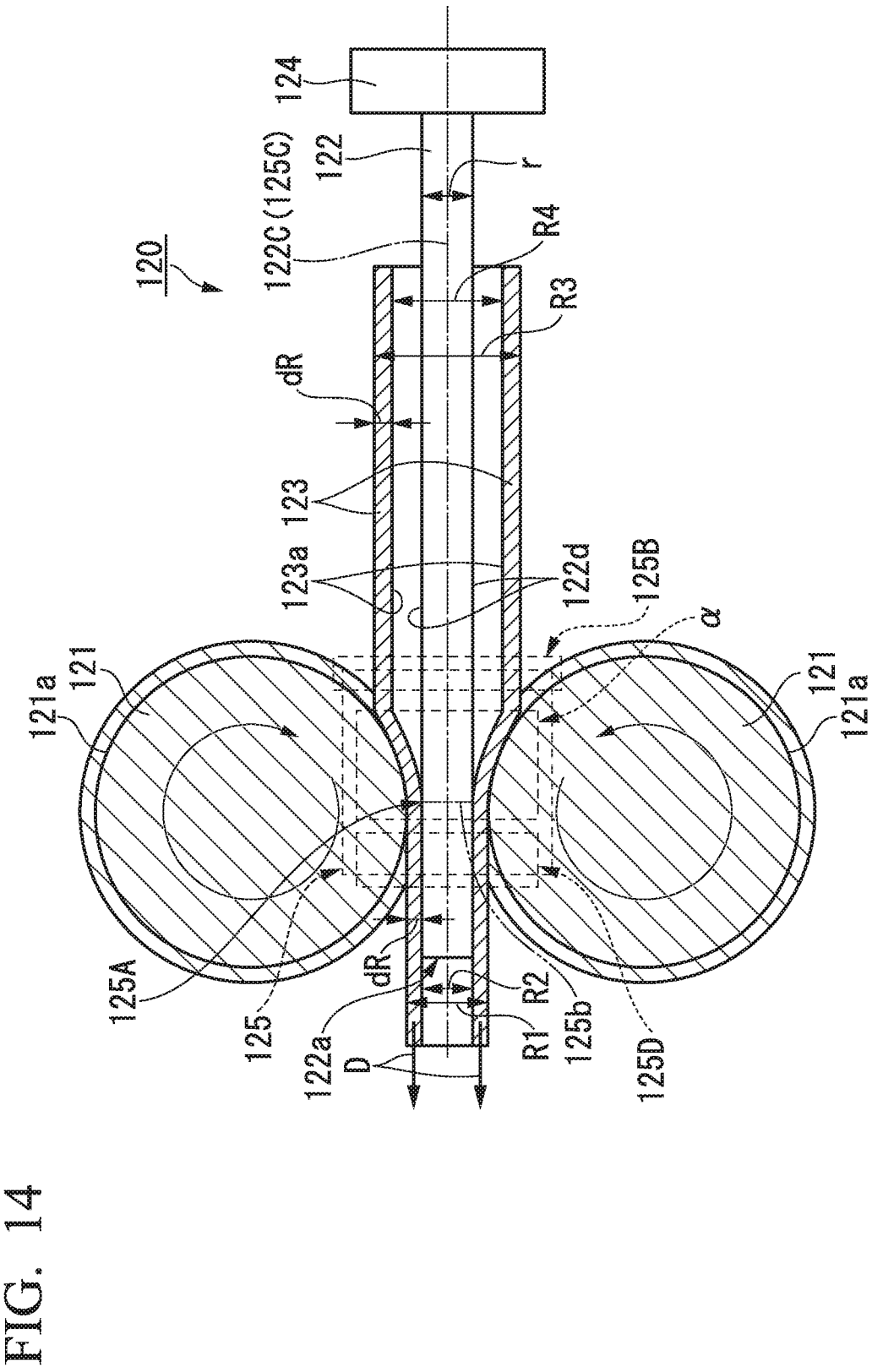
FIG. 14 is a view schematically showing the configuration of a drawing apparatus according to a modification example of the first embodiment of the present invention.

In the configuration of the drawing apparatus described above, an example of a case in which a roll is used as the first means 101 and a mandrel is used as the second means 102 will be described with reference to FIG. 14. FIG. 14 is a cross-sectional view of a drawing apparatus 120 taken along a plane parallel to a drawing direction D of a round tube 123 to be processed. The drawing apparatus 120 includes a plurality of rolls 121, a mandrel 122, and a fixing tool 124 of the mandrel.

In the roll (first means) 121, a semicircular groove 121a which is perpendicular to the rotational direction is continuously formed. The diameter of the semicircular groove is appropriately adjusted so that the round tube can be processed to have a desired outer diameter.

In a space 125 interposed between the groove 121a of each of the rolls and the groove 121a of the opposite roll 121, a part α which surrounds the round tube while being in contact therewith in the circumferential direction to reduce the diameter thereof is provided. The distance between the grooves 121a in a minimum inner diameter portion 125A of the part α is substantially equal to a final outer diameter R1 of the round tube.

The distance between the grooves 121a in an opening 125B on the inlet side of the round tube 123 is preferably larger than the outer diameter R3 of the round tube before being processed, and more preferably, is gradually reduced toward the minimum inner diameter portion 125A from the opening 125B. In addition, the distance between the grooves 121a in an opening 125D on the outlet side of the round tube 123 may be equal to or larger than the final outer diameter R1 of the round tube. The same effect can be obtained even when any of the die and the roll is used as the first means 101. Hereinafter, an example of the case of using the die will be described.

The mandrel (second means) 102 is disposed inside the round tube 103 having a final thickness dR and is disposed to oppose the minimum inner diameter portion 105A of the first means so that a side surface 102d thereof supports an inner wall surface 103a of the round tube. In addition, the mandrel 102 is a cylindrical member which is integrally molded to extend parallel to the drawing direction D of the round tube 103, and is preferably processed to have a strength such that the shape thereof can be maintained during the drawing of the round tube 103.

A center axis 102C of the mandrel in the longitudinal direction substantially coincides with a center axis 105C of the through-hole. Both the center axes 102C and 105C are configured to be perpendicular to one surface 105b which is formed by a portion that comes into contact with the round tube 103 in the minimum inner diameter portion 105A.

The thickness of the round tube is not changed before and after the drawing. That is, both the difference (R3−R4) between the outer diameter R3 and the inner diameter R4 of the round tube before the processing and the difference (R1−R2) between the outer diameter R1 and the inner diameter R2 of the round tube after the processing are substantially equal to the final thickness dR. In addition, the difference between the minimum inner diameter R2 of the through-hole and the outer diameter r of the mandrel 102 is substantially equal to the final thickness dR of the round tube.

One end 102a of the mandrel includes means which protrudes from the minimum inner diameter portion 105A in the drawing direction D of the round tube 103 and retreats in the opposite direction to the drawing direction D. In addition, the round tube 103 and the mandrel 102 are separated from each other by sliding on each other as the drawing proceeds.

One end 102a of the mandrel functions as a part (protrusion) which supports the inner wall of the portion of the round tube 103 that passes through the minimum inner diameter portion 105A and maintains the drawing direction of the round tube 103 to be constant during the drawing of the round tube 103.

The other end 102b of the mandrel is preferably fixed by using the fixing tool 104 so as not to move as the drawing of the round tube 103 proceeds.

In addition, the round tube 103 to be processed is preferably made of crystals having a hexagonal crystal structure, and for example, an alloy containing magnesium, titanium, cobalt, zinc, yttrium, a rare earth element, zirconia, and the like may be employed.

In the drawing apparatus according to the first embodiment, the mandrel during the drawing of the round tube is configured so that one end includes a part which supports the inner wall of the round tube that passes through the minimum inner diameter portion of the through-hole, the other end is fixed, and the center axis in the longitudinal direction coincides with the center axis of the through-hole. Therefore, the drawing apparatus according to the present invention can move the round tube to be parallel to the longitudinal direction of the through-hole and the mandrel.

With this configuration, in the drawing procedure, the entire outer wall surface of the round tube and the entire inner wall surface of the round tube are respectively pressed against the inner wall surface of the through-hole and the outer wall surface of the mandrel with equal forces. In addition, by adjusting the drawing rate of the round tube, the round tube can be processed to have desired outer and inner diameters with good precision over the entire region in the longitudinal and circumferential directions.

Furthermore, according to the configuration of the drawing apparatus of the present invention, since the inner wall surface of the through-hole is separated from the outer wall surface of the mandrel by the final thickness of the round tube during the drawing of the round tube, the thickness of the round tube does not become smaller than that before the processing. Therefore, the thickness of the round tube can be maintained before and after the drawing, and thus the deformation of the round tube due to a reduction in thickness as in the related art can be avoided. Accordingly, the round tube can be controlled to have desired outer and inner diameters with good precision over the entire region in the longitudinal and circumferential directions.

Moreover, according to the configuration of the drawing apparatus of the present invention, since the other end of the mandrel is fixed, only the round tube can be drawn by being separated from the mandrel. Therefore, the deformation of the wall portion of the round tube by further drawing out the mandrel from the round tube after the drawing using the die as in the mandrel drawing of the related art can be avoided.

[Drawing Method]

Figure 2A:
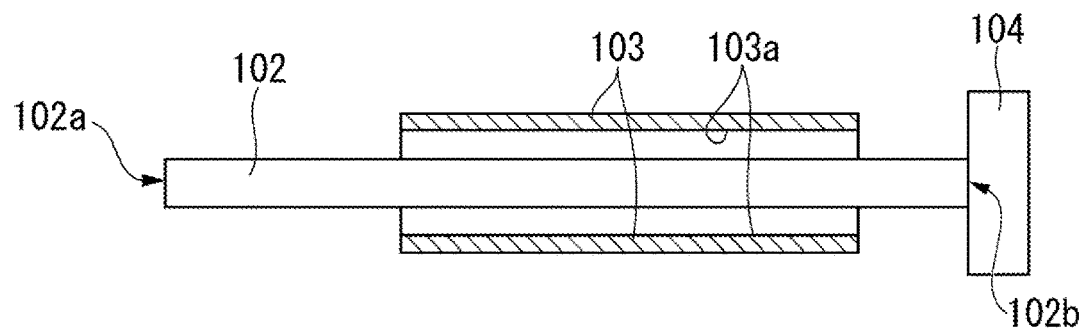
FIG. 2A is a view showing a first step of a drawing method using the drawing apparatus of FIG. 1.
Figure 2B:
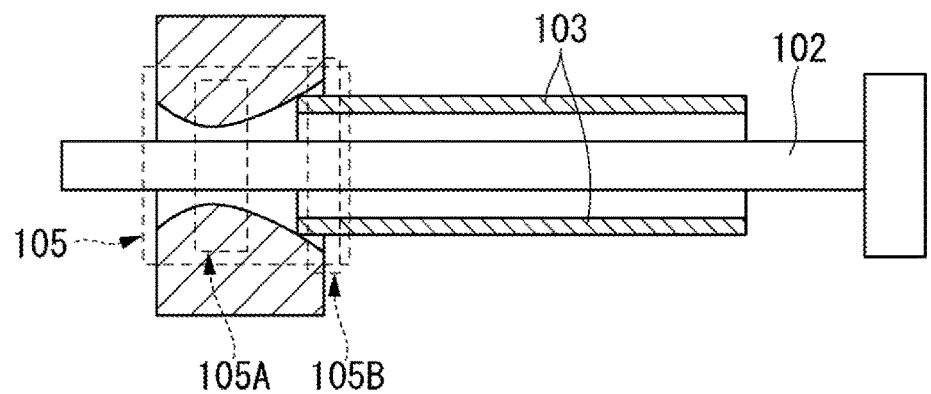
FIG. 2B is a view showing a second step of a drawing method according to the first embodiment of the present invention.
Figure 2C:
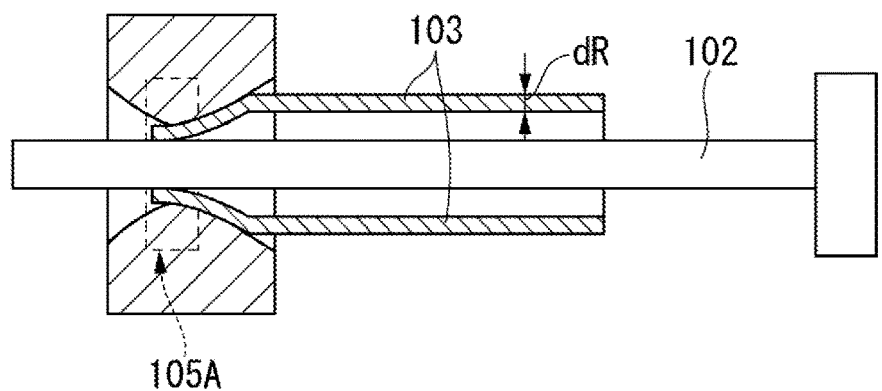
FIG. 2C is a view showing a third step of a drawing method according to the first embodiment of the present invention.

A drawing method of the round tube 103 performed by the drawing apparatus 100 shown in FIG. 1 will be described with reference to FIGS. 2A to 3B. FIGS. 2A to 2C are views showing the cross-sections of the main parts of the round tube and the drawing apparatus in stages according to the processing order in a procedure of performing a drawing process.

First, the round tube 103 having a desired thickness (final thickness dR) is manufactured by performing a hot extrusion process or a hot rolling process. The materials of the manufactured round tube 103 will be described with reference to Examples 1 to 3, which will be described later.

Next, the drawing process is performed by using the drawing apparatus 100 of FIG. 1 (process A). The drawing process includes three steps. That is, as a first step, as shown in FIG. 2A, the mandrel 102 is inserted into a space surrounded by the inner wall surface 103a of the round tube 103. One end 102a of the mandrel protrudes outward from the round tube 103, and the other end 102b of the mandrel is fixed to the fixing tool 104.

Subsequently, as a second step, as shown in FIG. 2B, the round tube 103 is inserted toward the minimum inner diameter portion 105A from the opening 105B on one side of the through-hole 105 along with the mandrel 102.

Figure 3A:
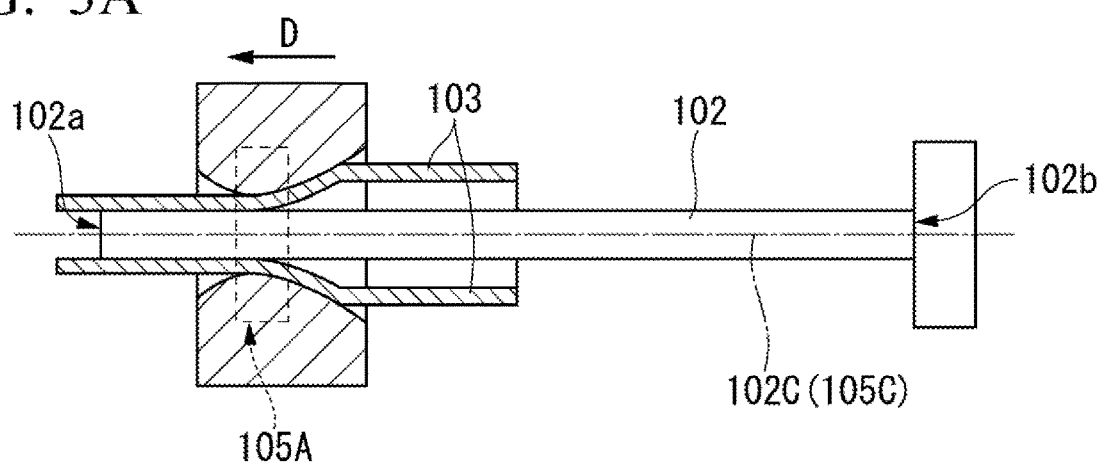
FIG. 3A is a view showing a stage following a stage illustrated in FIG. 2C of the drawing method according to the first embodiment of the present invention.

Subsequently, as a third step, as shown in FIG. 2C, the round tube 103 is inserted into the minimum inner diameter portion 105A of the through-hole, and while narrowing the round tube 103 to maintain the thickness dR, the mandrel 102 is allowed to retreat in the opposite direction to the drawing direction D of the round tube 103 as shown in FIG. 3A, thereby drawing only the round tube 103 from the minimum inner diameter portion 105A. At least in the third step, one end 102a of the mandrel is allowed to protrude outward from the minimum inner diameter portion 105A of the through-hole, the other end 102b of the mandrel is fixed, and the center axis 102C of the mandrel is allowed to substantially coincide with the center axis 105C of the through-hole.

Figure 3B:
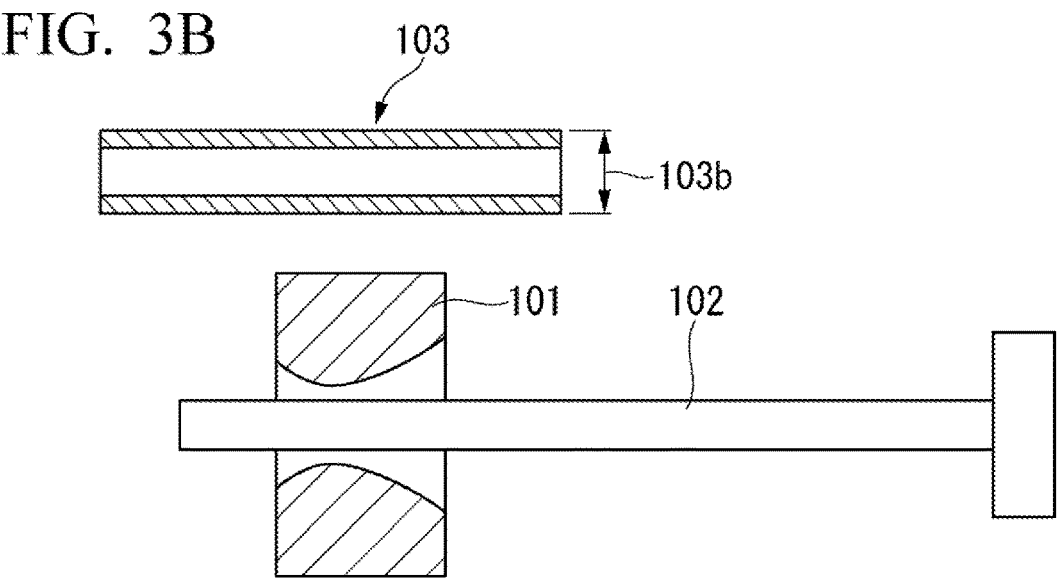
FIG. 3B is a view showing a stage following a stage illustrated in FIG. 3A of the drawing method according to the first embodiment of the present invention.

In addition, at the time when the round tube 103 is completely drawn from the die 101, as shown in FIG. 3B, the round tube 103 is in a state of being separated from the mandrel 102. Thereafter, the process A is repeated until an outer diameter 103b of the round tube becomes a desired outer diameter and an inner diameter.

Here, before and after the drawing process in the process A, it is preferable that the drawing rate is adjusted to allow the maximum reduction in the area of the cross-section (reduction in the cross-sectional area) of the round tube 103, which is perpendicular to the longitudinal direction, to be 14.3 [%] or higher and 15.4 [%] or less, and it is more preferable that the drawing rate is adjusted to allow the maximum reduction in the cross-sectional area to be 6 [%] or less.

In addition, it is preferable that a heating (annealing) treatment is performed on the round tube 103 subjected to the drawing process in the process A (process B). By performing the heating treatment, an effect of relieving strain introduced by the drawing process can be obtained. In a case of performing the process B, the process A and the process B are repeatedly performed until the outer diameter 103b of the round tube reaches a desired size.

By performing the above-described processes, the round tube 103 can be processed to have desired outer and inner diameters with good precision over the entire region in the longitudinal and circumferential directions while maintaining the thickness dR. Graphs for comparison between the outer diameter shapes of the round tube (narrow tube) 105 after the drawing, which are obtained by performing the above-described process of the present invention and the process by the mandrel drawing of the related art are shown in FIGS. 4 to 8.

Figure 4:
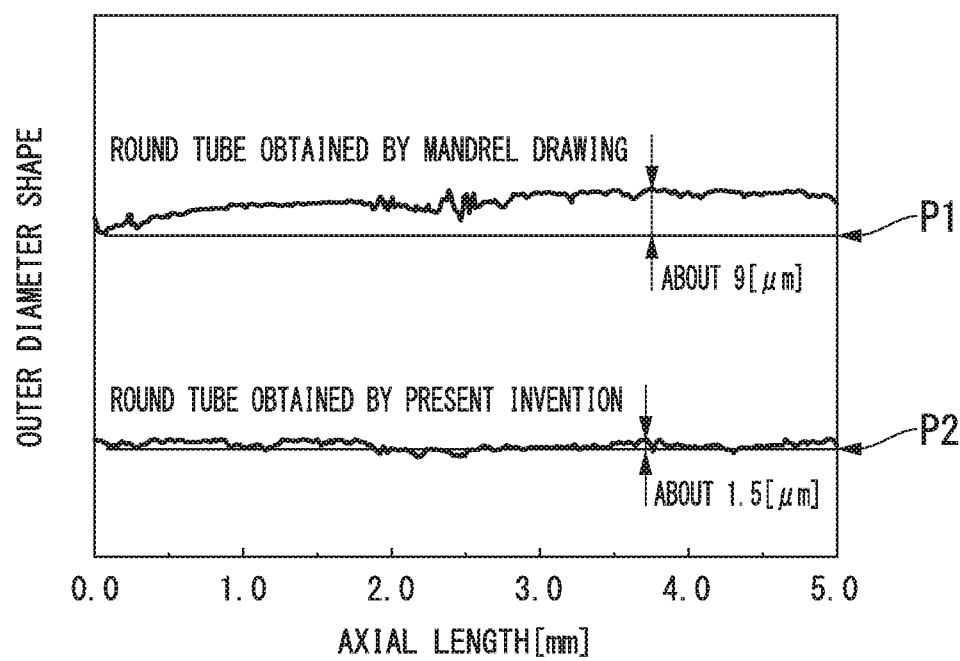
FIG. 4 is a graph for comparison in outer diameter shape between narrow tubes obtained according to the invention and the related art.

The two graphs of FIG. 4 illustrate the relationship between the position of the round tube 103 in the longitudinal direction (corresponding to the axial length in the horizontal axis of the graph) and the magnitudes of deviations (unevenness) from target positions P1 and P2 of the outer wall surface of the round tube 103 (corresponding to the outer diameter shape in the vertical axis of the graph). The upper graph corresponds to the result by the related art, and the lower graph corresponds to the result by the present invention.

In the outer diameter shape obtained by the related art, a deviation from the target position P1 occurs, and the maximum deviation is about 9 [μm]. On the other hand, in the outer diameter shape obtained by the present invention, a deviation from the target position P2 is suppressed within about 1.5 [μm], and thus it can be considered that a deviation rarely occurs compared to the case of the related art. From this result, according to the drawing method of the present invention, it is seen that the outer diameter of the round tube as designed can be obtained along the longitudinal direction with high precision, which cannot be obtained by the related art.

Figure 5:
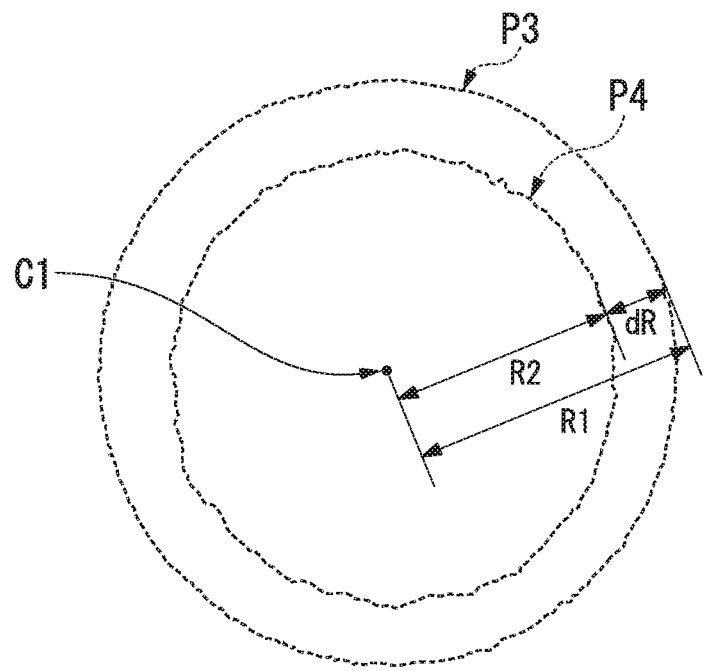
FIG. 5 is a view schematically showing the cross-sectional shape of the narrow tube obtained by the related art.

The graph of FIG. 5 illustrates the relative positional relationship between a center axis C1, an outer wall surface P3, and an inner wall surface P4 in the round tube which is subjected to the drawing (mandrel drawing) according to the related art so that the outer diameter is processed (reduced) from 2 [mm] to 1.5 [mm]. Here, as the round tube, a round tube made of an alloy of magnesium and calcium was used, and the thickness of the round tube before the drawing was 173 [μm].

Figure 6:
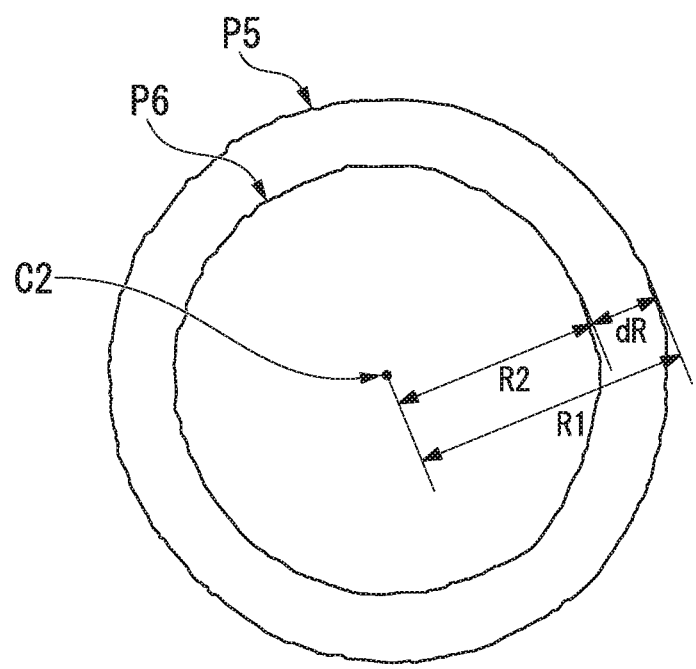
FIG. 6 is a view schematically showing the cross-sectional shape of the narrow tube obtained by the present invention.

The graph of FIG. 6 illustrates the relative positional relationship between a center axis C2, an outer wall surface P5, and an inner wall surface P6 in the round tube which is subjected to the drawing according to the present invention so that the outer diameter is processed (reduced) from 2 [mm] to 1.5 [mm]. Here, as the round tube, a round tube made of an alloy of magnesium and calcium was used, and the thickness of the round tube before the drawing was 173 [μm].

Figure 7:
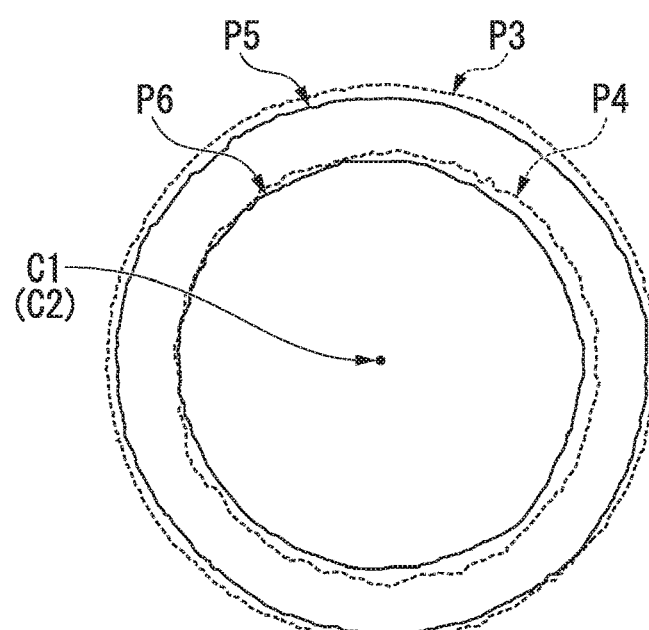
FIG. 7 is a view for comparison in cross-sectional shape between the narrow tubes obtained by the present invention and the related art.

In FIG. 7, the figures shown in FIGS. 5 and 6 are overlapped so that the center axes C1 and C2 coincide with each other. In the cross-section of the narrow tube manufactured by the present invention (indicated by solid line), both the outer wall surface P5 and the inner wall surface P6 are substantially uniform in the circumferential direction and have the shapes close to true circles. On the other hand, in the cross-section of the narrow tube manufactured by the related art (indicated by broken line), both the outer wall surface P3 and the inner wall surface P4 have variations (are uneven) in the circumferential direction and are formed to be greater than those in the case of the present invention in the diameter direction.

Figure 8:
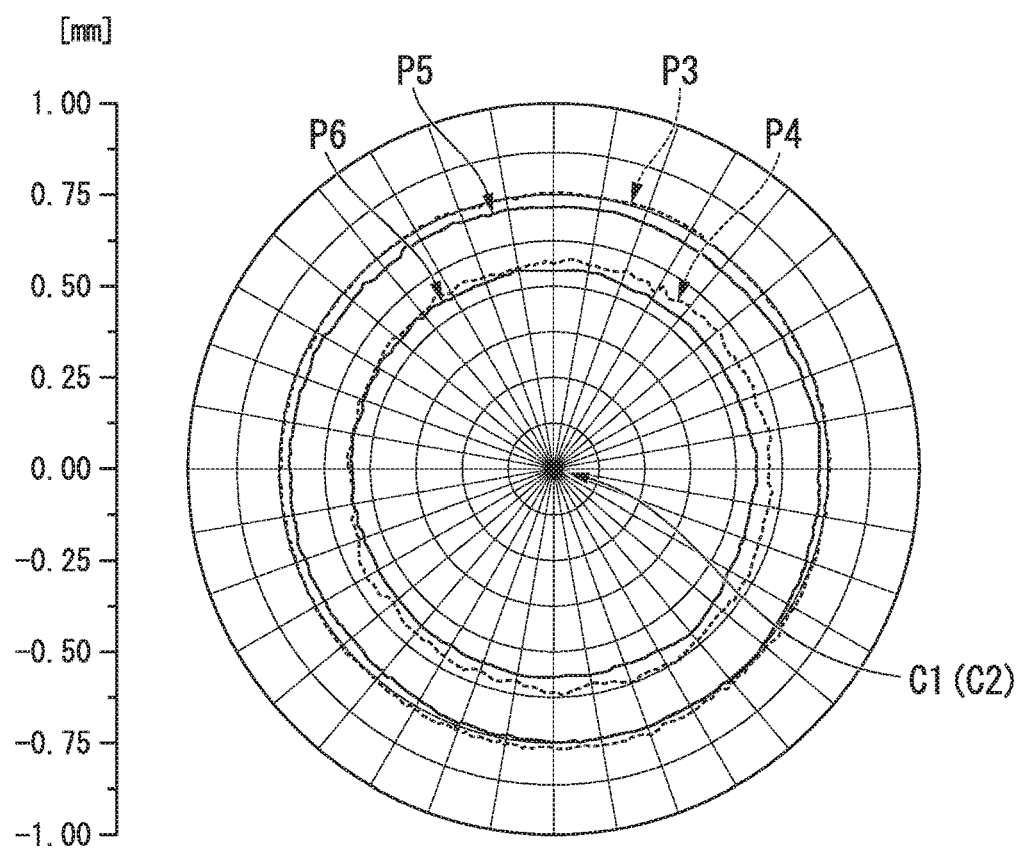
FIG. 8 is a view for comparison in cross-sectional shape between the narrow tubes obtained by the present invention and the related art using a graph.

In FIG. 8, for quantitative comparison between the dimensions of the cross-sections of the narrow tubes obtained by the present invention and the related art, which are shown in FIG. 7, the figures are shown to overlap a graph which radially extends from the origin. Since both the center axes C1 and C2 of the narrow tubes overlap the origin of the graph, a distance from the origin of the graph corresponds to the radius of the cross-section of the narrow tube.

In the case of the related art (broken line), when the mandrel (metal core) is drawn out from the round tube after the drawing by the die, as shown in the graph of FIG. 8, the outer diameter R1 and the inner diameter R2 of the round tube were respectively increased by about 2% and 2.5%. Accordingly, there was a tendency of the thickness dR of the round tube 103, that is, the difference R1-R2 between the outer diameter and the inner diameter after the drawing, to vary in the circumferential direction within a range of 130 to 200 [μm].

In addition, in the case of the present invention (solid line), since the mandrel drawing is not performed on the round tube after the drawing by the die 101 unlike in the related art, as shown in the graph of FIG. 8, the outer diameter R1 and the inner diameter R2 of the round tube after the drawing by the die were maintained. Therefore, the thickness dR of the round tube after the drawing according to the present invention, that is, the difference R1-R2 between the outer diameter and the inner diameter after the drawing, could be substantially uniformly maintained at 170 [μm] along the circumferential direction.

EXAMPLES

Hereinafter, the present invention will be described in more detail by using Examples 1 to 3 and Experimental Examples 1 to 4 corresponding to the first embodiment, but Examples to which the present invention can be applied are not limited to the Examples 1 to 3.

Example 1

The Example 1 of the above-described drawing apparatus will be described. A crucible made of graphite for high-frequency induction heating, which accommodates a mixture of pure magnesium metal (350 [g]) and pure calcium metal (2.8 [g]) was placed inside a high-frequency coil in a high-frequency melting furnace chamber. Next, the inside of the chamber was evacuated, and then was filled with helium gas to atmospheric pressure. Subsequently, the crucible was heated to 750 [° C.] and then was held for 10 minutes after checking that the accommodated mixture was melted. Thereafter, the mixture (molten alloy) which was melted in the crucible was poured into a cylindrical type mold which was placed on the front surface of the high-frequency coil in advance. In addition, after cooling the resultant for a certain time, a cylindrical alloy ingot was obtained from the mold.

Next, the obtained alloy ingot was processed into a bar having an outer diameter of 17 [mm] through hot extrusion under the conditions of a temperature of 400 [° C.] and an extrusion ratio of 15. In addition, a billet having an outer diameter of 10 [mm] was cut from the bar and then was subjected to hot extrusion under the conditions of a temperature of 400 [° C.] and an extrusion ratio of 42, thereby obtaining a round tube having an outer diameter of 3 [mm] and a thickness of 200 [μm].

Next, a long mandrel (of steel having a rigidity of 206 [GPa] and a tensile strength of 1900 [MPa]) of which one end was fixed was inserted into the obtained round tube. In addition, the round tube was inserted into a die along with the mandrel, and a drawing process was performed thereon. Before and after the drawing process, the reduction in the area of the cross-section of the round tube, which was perpendicular to the longitudinal direction, was adjusted to be 3.7 to 7.7 [%]. Here, the drawing process was performed in the atmosphere at room temperature. After the drawing process, an annealing treatment was performed at 300 [° C.] for 1 [h]. By performing the above process, a long, thin tube made of the magnesium-calcium alloy with an outer diameter of 1.5 [mm], a thickness of 200 [μm], and a length of 300 [mm] was obtained.

Example 2

The Example 2 of the above-described drawing apparatus will be described. A crucible made of graphite for high-frequency induction heating which accommodates a mixture of pure magnesium metal (350 [g]) and pure calcium metal (2.8 [g]) was placed inside a high-frequency coil in a high-frequency melting furnace chamber. Next, the inside of the chamber was evacuated, and then was filled with helium gas to atmospheric pressure. Subsequently, the crucible was heated to 750 [° C.] and then was held for 10 minutes after checking that the accommodated mixture was melted. Thereafter, the mixture (molten alloy) which was melted in the crucible was poured into a cylindrical type mold which was placed on the front surface of the high-frequency coil in advance. In addition, after cooling the resultant for a certain time, a cylindrical alloy ingot was obtained from the mold.

Next, the obtained alloy ingot was processed into a bar having an outer diameter of 17 [mm] through hot extrusion under the conditions of a temperature of 400 [° C.] and an extrusion ratio of 15. In addition, a billet having an outer diameter of 10 [mm] was cut from the bar and then was subjected to hot extrusion under the conditions of a temperature of 400 [° C.] and an extrusion ratio of 57, thereby obtaining a round tube having an outer diameter of 2.9 [mm] and a thickness of 150 [μm].

Next, a long mandrel (of steel having a rigidity of 206 [GPa] and a tensile strength of 1900 [MPa]) of which one end was fixed was inserted into the obtained round tube. In addition, the round tube was inserted into a die along with the mandrel, and a drawing process was performed thereon. Before and after the drawing process, the reduction in the area of the cross-section of the round tube, which was perpendicular to the longitudinal direction, was adjusted to be 3.9 to 5.6 [%]. Here, the drawing process was performed in the atmosphere at room temperature. After the drawing process, an annealing treatment was performed at 300 [° C.] for 1 [h]. By performing the above process, a long, thin tube made of the magnesium-calcium alloy with an outer diameter of 2.0 [mm], a thickness of 150 [nm], and a length of 350 [mm] was obtained.

Example 3

The Example 3 of the above-described drawing apparatus will be described. Billets having an outer diameter of 10 [mm] were cut from extruded bars AZ31 and WE43 made of a commercially available magnesium alloy and then were subjected to hot extrusion under the conditions of a temperature of 400 [° C.] and an extrusion ratio of 42, thereby obtaining round tubes having an outer diameter of 3.1 [mm] and a thickness of 250 [μm]. The bar AZ31 used here contained 96 [mass %] of magnesium, 3 [mass %] of aluminum, and 1 [mass %] of zinc. In addition, the bar bar WE43 used here contained 92.8 [mass %] of magnesium, 4 [mass %] of yttrium, 3 [mass %] of a rare earth element, and 0.2 [mass %] of zirconia.

Next, a long mandrel (of steel having a rigidity of 206 [GPa] and a tensile strength of 1900 [MPa]) of which one end was fixed was inserted into the obtained round tube. In addition, the round tube was inserted into a die along with the mandrel. The resultant was inserted into the obtained round tube. In addition, the round tube was inserted into a die along with the mandrel, and a drawing process was performed thereon. Before and after the drawing process, the reduction in the area of the cross-section of the round tube, which was perpendicular to the longitudinal direction, was adjusted to be 5.6 [%].

Here, the drawing process was performed in the atmosphere at room temperature. After the drawing process, an annealing treatment was performed at 300 [° C.] for 1 [h]. By performing the above process, a long, thin tube made of the commercially available magnesium alloy with an outer diameter of 2.0 [mm], a thickness of 200 [μm], and a length of 300 [mm] was obtained.

Experimental Example 1

The Experimental Example 1 which was conducted by using the drawing method of the first embodiment will be described. The Experimental Example 1 evaluates the effect of the dimensions of a portion (protrusion) 102a of the mandrel that protrudes from the minimum inner diameter portion 105A in the drawing direction D of the round tube, on the straight-advancing ability of the round tube 103 that passes through the minimum inner diameter portion 105A in the above-described drawing procedure.

Figure 9A:
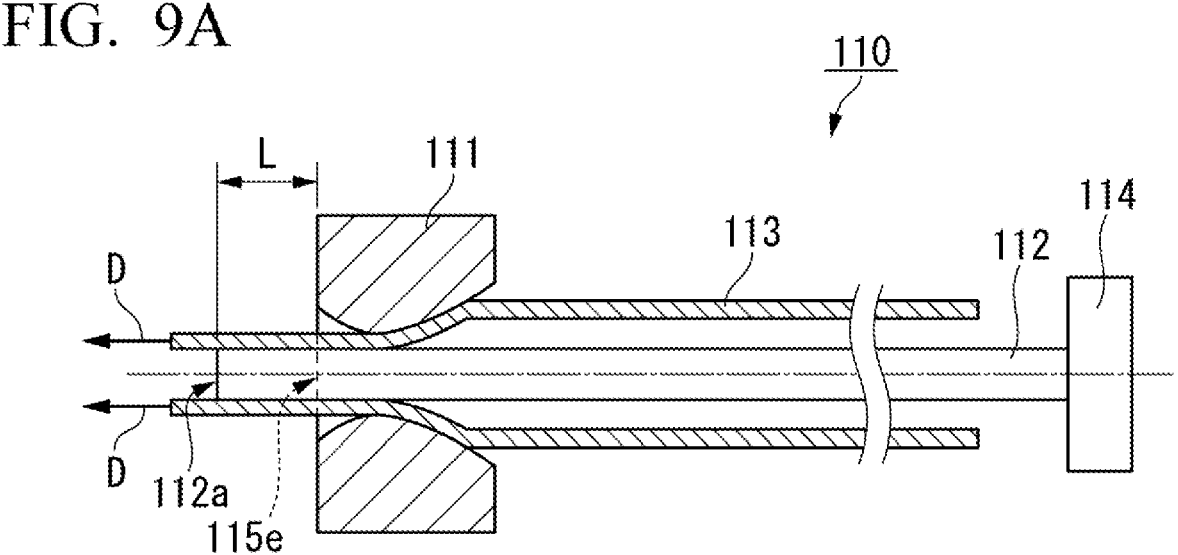
FIG. 9A is a view schematically showing the configuration of a drawing apparatus according to Experimental Example 1 of the present invention.

FIG. 9A is a cross-sectional view of a drawing apparatus 110 used in the Experimental Example 1, which is taken along a plane parallel to the drawing direction D of a round tube 113 to be processed. The drawing apparatus 110 includes a die 111, a mandrel 112, and a fixing tool 114 of the mandrel.

The experimental conditions will be described. As the die, a die having a length of 4.4 [mm] in the drawing direction was used. Machining oil was used as a lubricant between the die and the round tube and between the round tube and the mandrel, and the outer diameter of the round tube was processed (reduced) from 3 [mm] to 2.9 [mm] at a processing rate of 5 [mm/min].

Figure 9B:
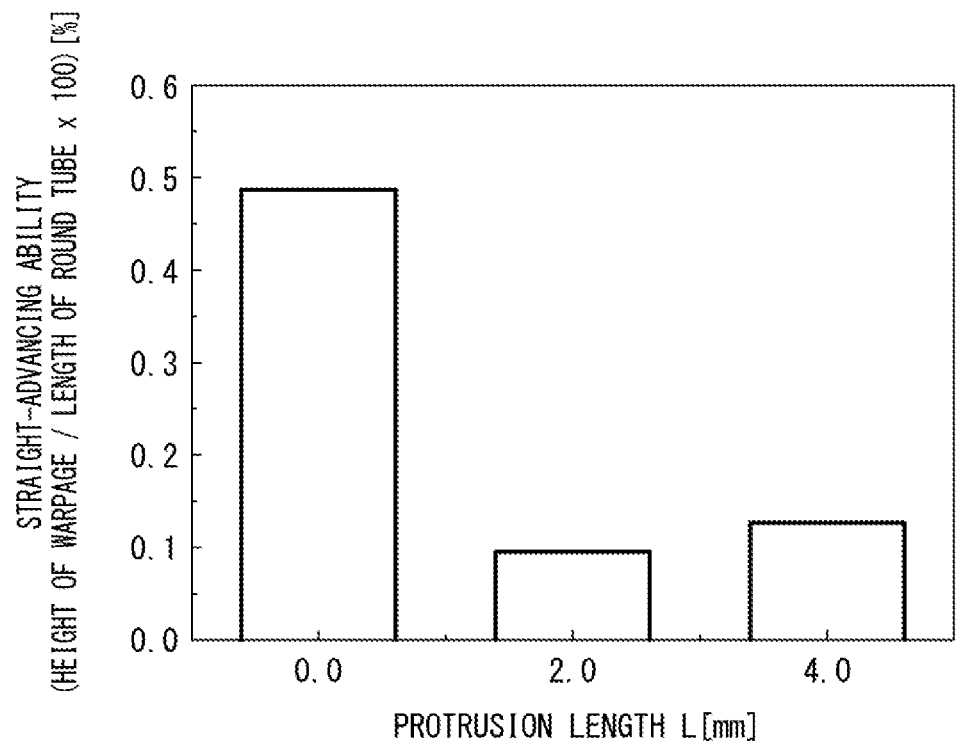
FIG. 9B is a graph showing the result of Experimental Example 1 of the present invention.

The graph of FIG. 9B shows the relationship between the protrusion length L (corresponding to the horizontal axis) of the mandrel 112 from the die 111 and the straight-advancing ability (corresponding to the vertical axis) of the round tube. Here, the protrusion length L is defined as the distance from an opening surface 115e of the die on the outlet side of the round tube to one end 112a of the mandrel. In addition, the straight-advancing ability is defined as the ratio of the height (magnitude) of warpage to the length of the round tube, that is, (the height of warpage/the length of the round tube×100).

As shown in the graph of FIG. 9B, in a case where the protrusion length L was 0.0 [mm], that is, in a case where one end 112a of the mandrel was positioned inside the die, the straight-advancing ability was 0.5 [%]. On the other hand, in a case where the protrusion length L was 2.0 [mm] and 4.0 [mm], that is, in a case where the mandrel 112 had protruded outward from the opening surface 115e of the die to the positions distant therefrom by 2.0 [mm] and 4.0 [mm], the straight-advancing ability was 0.1 [%] and 0.12 [%]. From the results, it was seen that, by allowing the mandrel 112 to protrude outward by about 2.0 to 4.0 [mm], the magnitude of warpage of the round tube 113 after the drawing could be suppressed to be about one-fifth of that in a case where the mandrel 112 did not protrude.

Experimental Example 2

The Experimental Example 2 which was conducted by the drawing apparatus and the processing method of the first embodiment will be described. The Experimental Example 2 compares the thicknesses of the round tube 103 before and after the above-described drawing.

The experimental conditions will be described. Machining oil was used as a lubricant between the die and the round tube and between the round tube and the mandrel, and the outer diameter of the round tube was processed (reduced) from 2.0 [mm] to 1.9 [mm] at a processing rate of 10 [mm/min].

Figure 10:
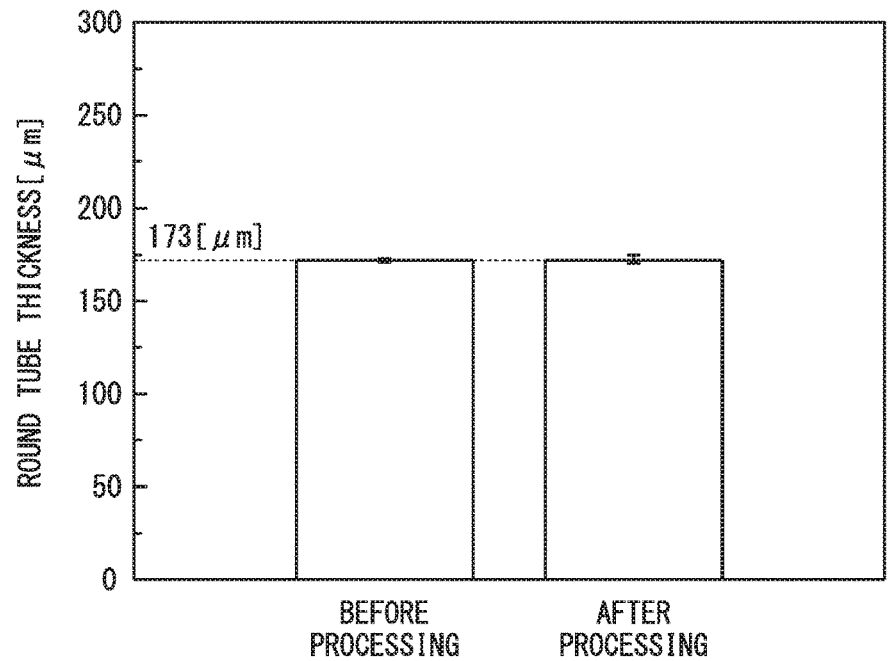
FIG. 10 is a graph showing the result of Experimental Example 2 of the present invention.

FIG. 10 is a graph showing the comparison between the thicknesses of the round tube 103 before and after the drawing. The vertical axis of the graph represents the thickness of the round tube. The horizontal axis of the graph represents a timing at which the thickness is measured, in which the left side corresponds to the result before the drawing and the right side corresponds to the result after the drawing.

As shown in the graph of FIG. 10, the thickness dR of the round tube before the drawing was 173±1 [μm], and the thickness dR of the round tube after the drawing was 173±6 [μm]. The difference between the thicknesses dR before and after the drawing was within a range of measurement error, and thus the thickness dR was rarely changed and consequently reached about 173 [μm]. From this result, it was seen that the reduction in the diameter of the round tube 103 by the drawing can be performed without changing the thickness dR of the round tube, by using the drawing apparatus 100 and the method of the present invention.

Experimental Example 3

The Experimental Example 3 which was conducted by using the drawing apparatus and the processing method of the first embodiment will be described. The Experimental Example 3 examines limitations (processing limitations) regarding a reduction in the area of the cross-section of the round tube 103, which is perpendicular to the longitudinal direction, during a single drawing process.

The experimental condition will be described. Machining oil was used as a lubricant between the die 101 and the round tube 103 and between the round tube 103 and the mandrel 102. As the round tube 103, a round tube obtained by extruding an alloy having a diameter of 1.5 to 3 [mm] and containing 0.8 mass % of calcium at 450° C. and processing the thickness dR of the round tube into a final thickness was used. Regarding the processing rate during the drawing, two cases of a processing rate of 5 [mm/min] and a processing rate of 10 [mm/min] were examined.

Figure 11:
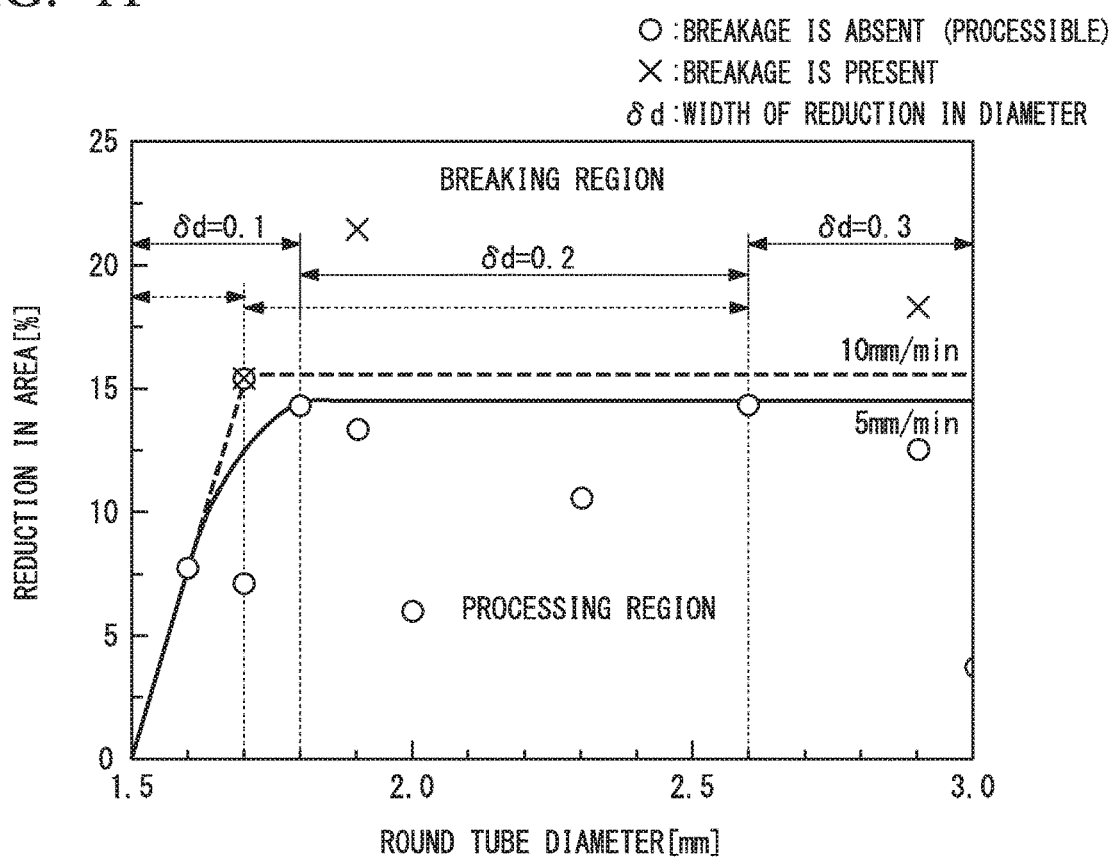
FIG. 11 is a graph showing the result of Experimental Example 3 of the present invention.

FIG. 11 is a graph showing the processing limitations regarding the reduction in the area of the round tube 103 during a single drawing process. The vertical axis of the graph represents the reduction in area. The horizontal axis of the graph represents the diameter (tube diameter) of the round tube 103 before the drawing. The solid line curve in the graph corresponds to the case of a processing rate of 5 [mm/min], and the broken line curve in the graph corresponds to the case of a processing rate of 10 [mm/min].

In addition, according to the tube diameter of the round tube 103 before the drawing, the width 8d of a reduction in diameter by the drawing was adjusted. That is, at a processing rate of 5 [mm/min], the reduction in diameter was 0.1 [mm] (δd=0.1) in a case where the tube diameter was 1.5 to 1.8 [mm] before the drawing of the round tube 103, the reduction in diameter was 0.2 [mm] (δd=0.2) in a case where the tube diameter was 1.8 to 2.6 [mm], and the reduction in diameter was 0.3 [mm] (δd=0.3) in a case where the tube diameter was 2.6 to 3.0 [mm].

In addition, at a processing rate of 10 [mm/min], the reduction in diameter was 0.1 [mm] (δd=0.1) in a case where the tube diameter was 1.5 to 1.7 [mm] before the drawing of the round tube 103, the reduction in diameter was 0.2 [mm] (δd=0.2) in a case where the tube diameter was 1.7 to 2.6 [mm], and the reduction in diameter was 0.3 [mm] (δd=0.3) in a case where the tube diameter was 2.6 to 3.0 [mm].

As shown in the graph of FIG. 11, in both the case where the tube diameter on the solid line curve was in a range of 1.5 to 1.8 [mm] and the case where the tube diameter on the broken line curve was in a range of 1.5 to 1.7 [mm], it was seen that the maximum reduction in area by which the breaking of the round tube 103 could be suppressed had a tendency to steeply increase in proportion to the tube diameter. In addition, in both the case where the tube diameter on the solid line curve was in a range of 1.8 to 3.0 [mm] and the case where the tube diameter on the broken line curve was in a range of 1.7 to 3.0 [mm], it was seen that the maximum reduction in area had a tendency to be constant regardless of the tube diameter. In addition, for the entire range of the tube diameter, it was seen that the maximum reduction in area in the case where the processing rate was 10 [mm/min] was greater than that in the case where the processing rate was 5 [mm/min].

In the case where the processing rate was 5 [mm/min], it was seen that processing of the round tube was possible only at a reduction in area in the region (processing region) below the broken line curve and the round tube was broken and thus processing was impossible at a reduction in area in the region (breaking region) above the broken line curve.

In addition, in the case where the processing rate was 10 [mm/min], it was seen that processing of the round tube was possible only at a reduction in area in the region (processing region) below the solid line curve and the round tube was broken and thus processing was impossible at a reduction in area in the region (breaking region) above the solid line curve.

From the results, it was seen that the maximum reduction in area was increased in proportion to the processing rate and thus the reduction in area in a single drawing process could be increased. Therefore, a round tube which was reduced in diameter to have desired dimensions could be obtained by a smaller number of drawing processes.

Experimental Example 4

The Experimental Example 4 which was conducted by using the drawing apparatus and the processing method of the first embodiment will be described. The Experimental Example 4 compares a processing force applied during the drawing of the round tube between the drawing method of the present invention and the drawing methods (floating plug method and metal core drawing method) of the related art.

The experimental conditions will be described. Machining oil was used as a lubricant between the die 101 and the round tube 103 and between the round tube 103 and the mandrel 102. As the round tube 103, a round tube obtained by extruding an alloy containing 0.8% of calcium at 450° C. and processing the thickness dR of the round tube into a final thickness was used.

Figure 12:
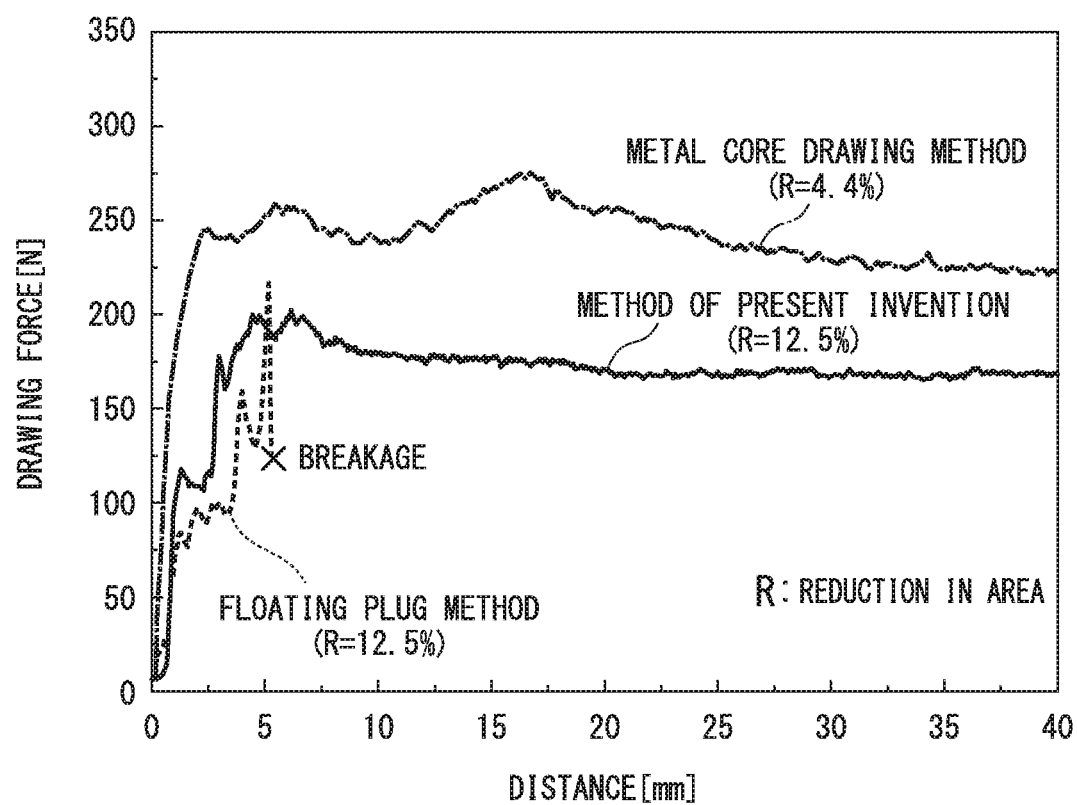
FIG. 12 is a graph showing the result of Experimental Example 4 of the present invention.
Figure 13A:
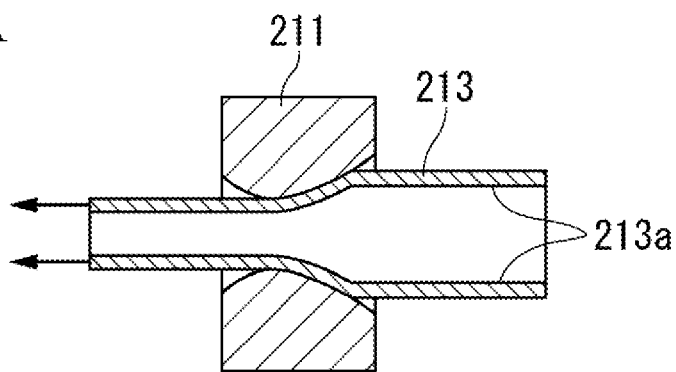
FIG. 13A is a view schematically showing the configuration of a drawing apparatus according to tube sinking.
Figure 13B:
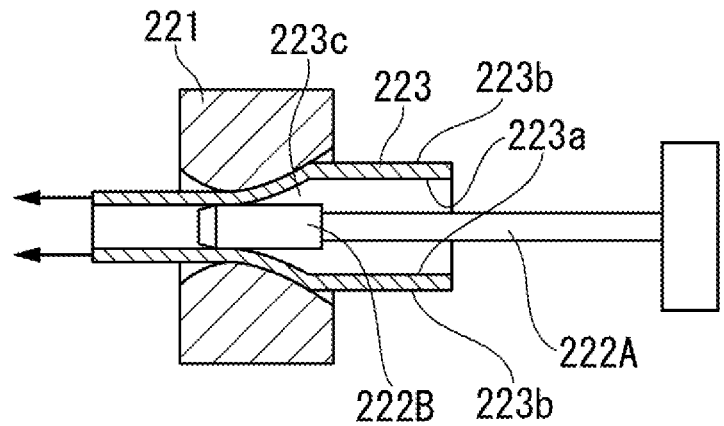
FIG. 13B is a view schematically showing the configuration of a drawing apparatus according to fixed plug drawing.
Figure 13C:
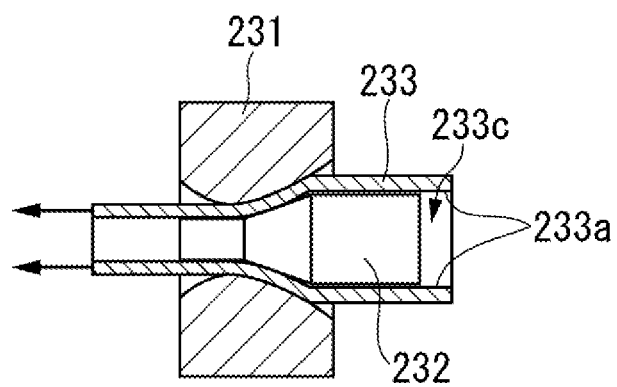
FIG. 13C is a view schematically showing the configuration of a drawing apparatus according to floating plug drawing.
Figure 13D:
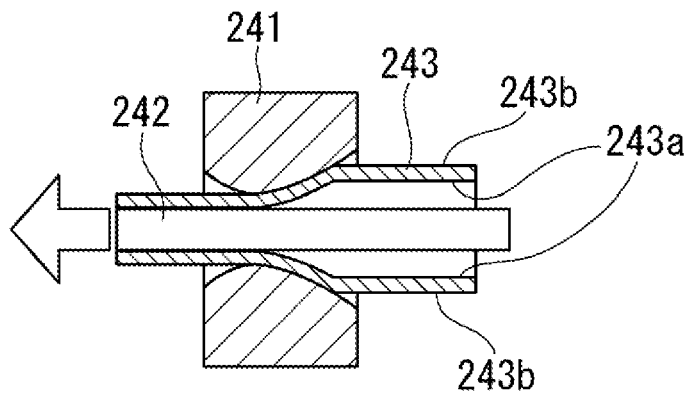
FIG. 13D is a view schematically showing the configuration of a drawing apparatus according to mandrel drawing.

FIG. 12 is a graph showing processing curves regarding the processing methods and the reduction in area of the round tube 103 in a single drawing process. The vertical axis of the graph represents the magnitude of the drawing force of the round tube, and the horizontal axis of the graph represents the length of the drawn portion of the round tube. The three curves of the graph correspond to, sequentially from above, a case of using the metal core drawing (mandrel drawing) method, a case of using the above-described drawing method of the present invention, and a case of using the floating plug drawing method.

As shown in the graph of FIG. 12, in the case of using the floating plug drawing method, when the drawing force was about 125 [N], breaking had occurred at a position away from the drawing starting position by about 5 [mm]. This is caused by a high processing force and low processing limitations in the floating plug drawing method. In addition, in the case of using the metal core drawing method, drawing was performed with a great force of about 250 [N] even at a low reduction in area R of 4.4%. On the other hand, in the case of using the drawing method of the present invention, even at a high reduction in area R of 12.5%, breaking did not occur during the drawing, and drawing with a force of about 70% of that in the case of using the metal core drawing method could be realized.

Experimental Example 5

Experimental Example 5 which was conducted by using the drawing apparatus and the processing method of the first embodiment will be described. The Experimental Example 5 compares a crystal orientation structure in the cross-section of the round tube after the processing between the case of using the drawing method of the present invention and the case of using the drawing methods (floating plug method and metal core drawing method) of the related art.

In the Experimental Example 5, four samples (Samples 1 to 4) made of an Mg alloy were used.

(Sample 1)
The Sample 1 is obtained by performing a heating treatment at 450° C. on a round tube having a tube diameter of 2 [mm] and a thickness of 173 [μm].

(Sample 2)
The Sample 2 is a round tube having a tube diameter of 1.9 [mm] and a thickness of 173 [μm] which is obtained by performing the drawing according to the present invention on a round tube having a tube diameter of 2 [mm] and a thickness of 173 [μm]. During the drawing, machining oil was used as a lubricant between the die and the round tube and between the round tube and the mandrel, and a processing rate was 10 [mm/min].

(Sample 3)
The Sample 3 is a round tube having a tube diameter of 1.5 [mm] and a thickness of 173 [μm] which is obtained by performing the drawing according to the present invention on a round tube having a tube diameter of 2 [mm] and a thickness of 173 [μm] and performing a heating treatment thereon at 300 [° C.] and for 1 [hour] after the drawing. During the drawing, machining oil was used as a lubricant between the die and the round tube and between the round tube and the mandrel, and a processing rate was 10 [mm/min].

(Sample 4)
The Sample 4 is a round tube having a tube diameter of 1.8 [mm] and a thickness of 443 [μm] which is obtained by performing the drawing according to the related art (metal core drawing) on a round tube having a tube diameter of 3 [mm] and a thickness of 0.7 [mm] and performing a heating treatment thereon at 300 [° C.] and for 1 [hour] after the drawing. During the drawing, machining oil was used as a lubricant between the die and the round tube and between the round tube and the mandrel, and the processing rate was 1 [mm/min].

All of the tubes of the Samples 1 to 4 were cut along a plane perpendicular to the axis by an electric discharge machine and were buried into a resin. Thereafter, the cross-sections thereof were polished by using emery papers #400, #600, #800, #1000, #2000, and #4000 in this order and the surfaces were finished by using alumina abrasive grains having sizes of 1 [μm] and 0.05 [μm] in this order. The finished surfaces of the samples were further polished by using an ion polishing device, and EBSD measurement was performed thereon.

FIGS. 15A to 15D are graphs respectively showing the orientations of the basal planes (0001) of the crystal structures (hexagonal crystal structures) of the Samples 1 to 4 in the TD direction and the RD direction. FIGS. 16A to 16D are image diagrams respectively showing the orientations of the crystal structures (hexagonal crystal structures) corresponding to FIGS. 15A to 15D.

Figure 16A:
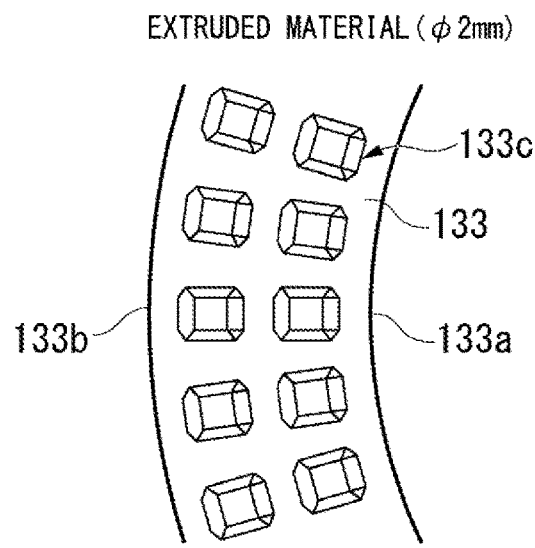
FIG. 16A is an image diagram regarding the result of Sample 1 of the Experimental Example 5.
Figure 16B:
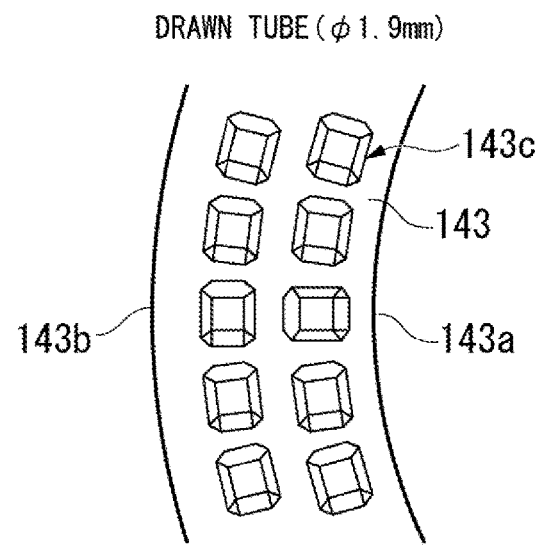
FIG. 16B is an image diagram regarding the result of Sample 2 of the Experimental Example 5.
Figure 16C:
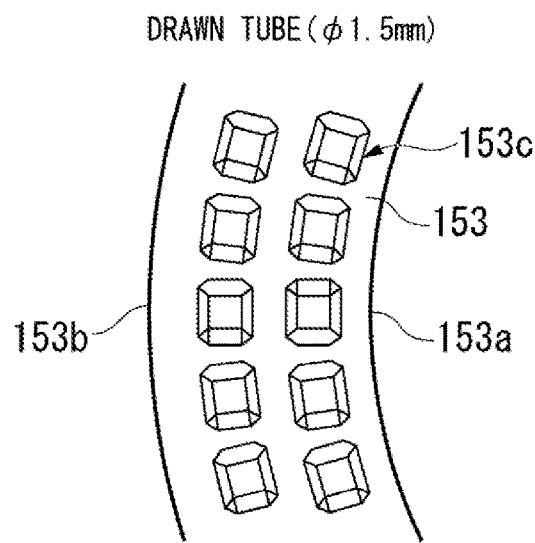
FIG. 16C is an image diagram regarding the result of Sample 3 of the Experimental Example 5.

As shown in the graphs of FIGS. 15B and 15C, the Samples 2 and 3 subjected to the drawing according to the present invention were inclined at 90 [°] with respect to the circumferential direction and were oriented along the circumferential direction. The states of the orientations at this time are shown in FIGS. 16B and 16C. That is, crystals 143c constituting a round tube 143 are uniformly oriented in a direction (circumferential direction) perpendicular to a direction from an inner surface 143a of the round tube to an outer surface 143b. In addition, crystals 153c constituting a round tube 153 are uniformly oriented in a direction (circumferential direction) perpendicular to a direction from an inner surface 153a of the round tube to an outer surface 153b.

As shown in the graph of FIG. 15A, the Sample 1 which was not subjected to the drawing was oriented in a direction (radial direction) from the axis of the round tube to the surface. The state of the orientation at this time is shown in FIG. 16A. That is, crystals 133c constituting a round tube 133 are uniformly oriented in a direction from an inner surface 133a of the round tube to an outer surface 133b.

As shown in the graphs of FIGS. 15B and 15C, the Samples 2 and 3 subjected to the drawing according to the present invention were inclined at 90 [°] with respect to the circumferential direction, and were oriented along the circumferential direction. The states of the orientations at this time are shown in FIGS. 16B and 16C. That is, the crystals 143c constituting the round tube 143 are uniformly oriented in the direction (circumferential direction) perpendicular to the direction from the inner surface 143a of the round tube to the outer surface 143b. In addition, crystals 153c constituting the round tube 153 are uniformly oriented in the direction (circumferential direction) perpendicular to the direction from the inner surface 153a of the round tube to the outer surface 153b.

Figure 16D:
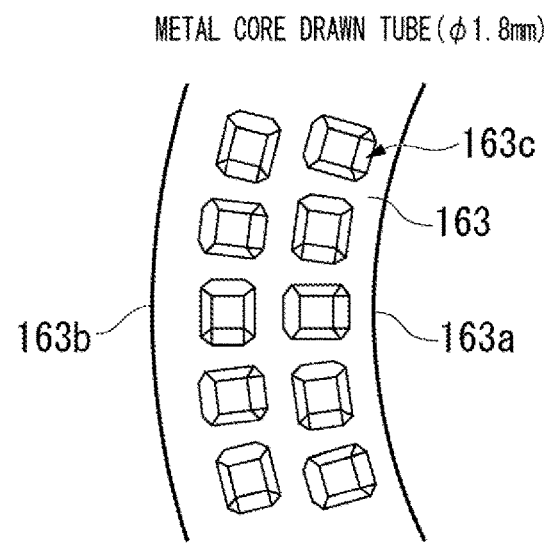
FIG. 16D is an image diagram regarding the result of Sample 4 of the Experimental Example 5.

As shown in the graph of FIG. 15D, the Sample 4 subjected to the drawing according to the related art was randomly oriented in the circumferential direction and the radial direction. The state of the orientation at this time is shown in FIG. 16D. That is, crystals 163c constituting a round tube 163 are randomly oriented in a direction (radial direction) from an inner surface 163a of the round tube to an outer surface 163b and in a direction (circumferential direction) perpendicular thereto.

Second Embodiment (A) Production of Samples

Figure 17:
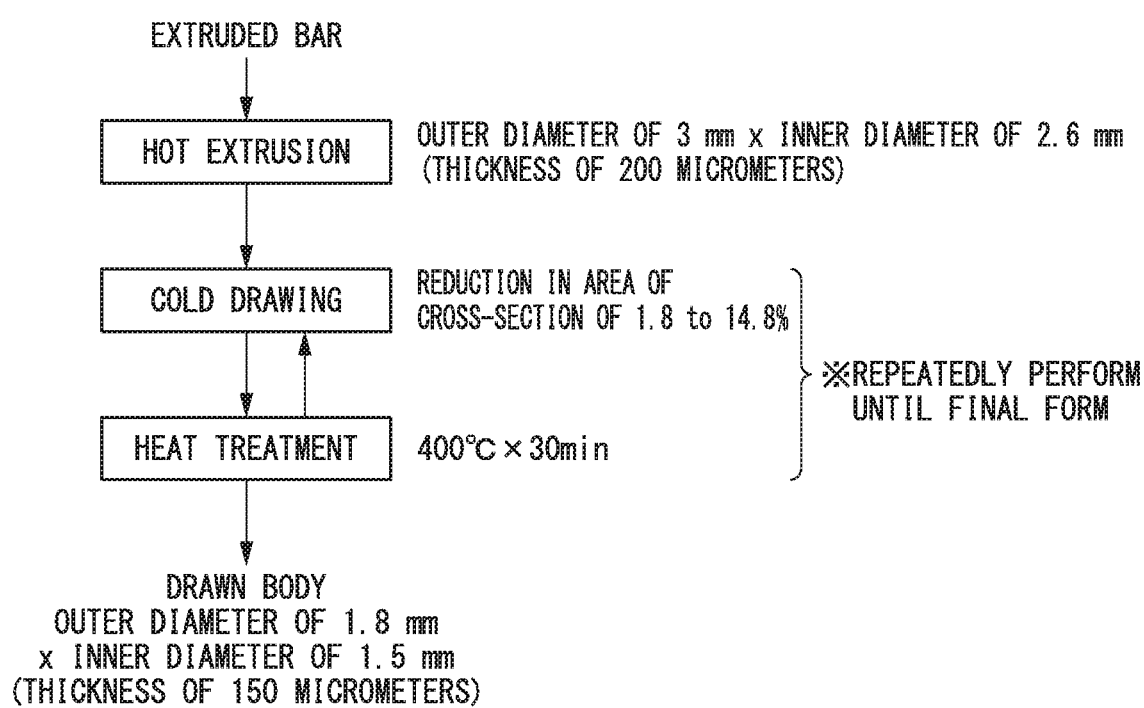
FIG. 17 is a flowchart showing a method of manufacturing a thin, narrow tube according to the present invention.

In this embodiment, a method of manufacturing thin, narrow tubes having different crystal orientations is studied. FIG. 17 is a flowchart showing the method of manufacturing thin, narrow tubes.

First, a billet having an outer diameter of 10 [mm] was cut from an extruded bar AZ31 made of a commercially available magnesium alloy and was subjected to hot extrusion under the conditions of a temperature of 450° C. and an extrusion ratio of 42, thereby obtaining an extruded round tube having an outer diameter of 3 [mm] and an inner diameter of 2.6 [mm] (a thickness of 200 [μm]) (hot extrusion). The composition of the extruded bar AZ31 used here includes 96 [mass %] of magnesium (Mg), 3 [mass %] of aluminum, and 1 [mass %] of zinc (Zn).

Next, a long mandrel was inserted into the obtained round tube, the round tube was inserted into a drawing die along with the mandrel, and a drawing process was performed thereon in the atmosphere at room temperature (cold drawing). The drawing was repeatedly performed by adjusting the reduction in the area of the cross-section of the round tube, which was perpendicular to the longitudinal direction, before and after the processing to be in a range of 1.8 to 14.8 [%] per each process and performing an annealing treatment (heat treatment) thereon at 400 [° C.] for 30 [min] after the processing until the final form of the drawn body had an outer diameter of 1.8 [mm] and an inner diameter of 1.5 [mm] (a thickness of 150 [μm]).

In addition, Samples 5 to 8 having different crystal orientation structures, which will be described later in detail, were obtained by performing different drawing methods in a final drawing process to obtain the final form. FIGS. 18A to 18D are views schematically showing the configurations of different drawing apparatuses.

(Sample 5)

Figure 18A:
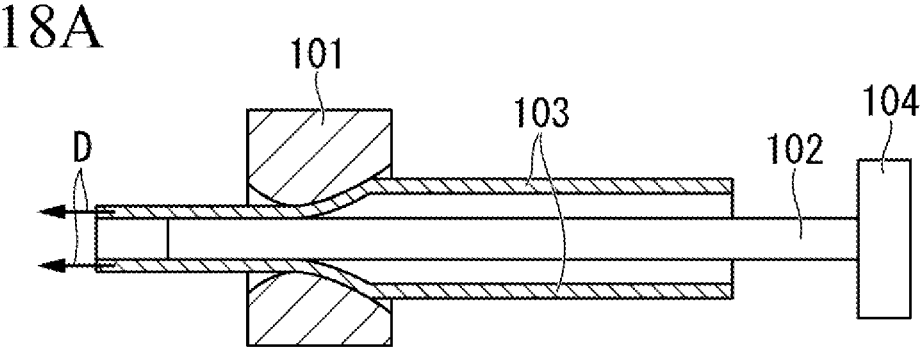
FIG. 18A is a view schematically showing a configuration of a fixed mandrel drawing apparatus.

The Sample 5 was produced by using a "fixed mandrel drawing" apparatus shown in FIG. 18A as the drawing method. In FIG. 18A, 101 denotes a die (first means), 102 denotes a mandrel (second means), 103 denotes a round tube, and 104 denotes a fixing tool. D denotes the drawing direction of the round tube 103.

More specifically, the apparatus of FIG. 18A is a drawing apparatus which includes at least the first means 101 including a part α which surrounds the round tube 103 while being in contact therewith in the circumferential direction to reduce the diameter thereof, and the cylindrical second means 102 which is disposed to oppose a minimum inner diameter portion of the part α and of which the side surface supports the round tube, in which the center axis of the minimum inner diameter portion and the center axis of the second means coincide with the drawing direction of the round tube, the first means and the second means are separated from each other over the entire circumferences thereof by the thickness of the round tube, and the means (fixing tool) 104 for allowing one end of the second means to protrude from the minimum inner diameter portion in the drawing direction of the round tube and to retreat with respect to the movement of the round tube is included.

The drawing process was performed on the Sample 5 by inserting the long mandrel (of steel having a rigidity of 206 [GPa] and a tensile strength of 1900 [MPa]) of which one end was fixed, into the round tube which was processed to have an outer diameter of 1.9 [mm] and an inner diameter of 1.6 [mm] (a thickness of 150 [mil]) and was subjected to an annealing treatment at 400 [° C.] for 30 [min], inserting the round tube into the die along with the mandrel, and drawing out only the round tube in the atmosphere at room temperature. The processing was performed so that the reduction in the area of the cross-section of the round tube, which was perpendicular to the longitudinal direction, was 5.7 [%], and the thickness was not changed before and after the drawing process. After the drawing process, the annealing treatment was performed at 400 [° C.] for 30 [min]. By performing the above process, a long, thin, and narrow tube which was made of the AZ31 alloy and had an outer diameter of 1.8 [mm] and an inner diameter of 1.5 [mm] (a thickness of 150 [μm]) was obtained.

(Sample 6)

Figure 18B:
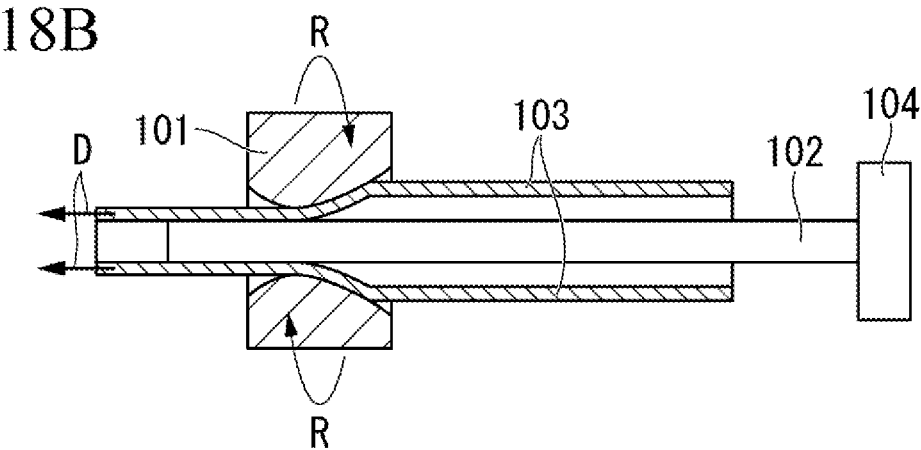
FIG. 18B is a view schematically showing a configuration of a rotating fixed-mandrel drawing apparatus.

The Sample 6 was produced by using a "rotating fixed-mandrel drawing" apparatus shown in FIG. 18B as the drawing method. The apparatus of FIG. 18B differs from the above-described apparatus of FIG. 18A in that the part α of the die (first means) 101 further includes means (not shown) for coming into contact with the outer surface of the round tube 103 which advances in the drawing direction D and rotating along the outer surface of the round tube. The other features are the same as those of the above-described apparatus of FIG. 18A.

In FIG. 18B, 101 denotes a die (first means), 102 denotes a mandrel (second means), 103 denotes a round tube, and 104 denotes a fixing tool. D denotes the drawing direction of the round tube 103, and R denotes a direction in which the die (first means) 101 rotates.

The drawing process was performed on the Sample 6 by inserting the long mandrel (of steel having a rigidity of 206 [GPa] and a tensile strength of 1900 [MPa]) of which one end was fixed, into the round tube which was processed to have an outer diameter of 1.9 [mm] and an inner diameter of 1.6 [mm] (a thickness of 150 [μm]) and was subjected to an annealing treatment at 400 [° C.] for 30 [min], inserting the round tube into the die along with the mandrel, and drawing out only the round tube in the atmosphere at room temperature while rotating the die. The processing was performed so that the reduction in the area of the cross-section of the round tube, which was perpendicular to the longitudinal direction, was 5.7 [%], and the thickness was not changed before and after the drawing process. The rotational speed of the die was 240 [rpm], and the drawing rate was 0.6 [mm/s]. After the drawing process, an annealing treatment was performed at 400 [° C.] for 30 [min]. By performing the above process, a long, thin, and narrow tube which was made of the AZ31 alloy and had an outer diameter of 1.8 [mm] and an inner diameter of 1.5 [mm] (a thickness of 150 [μm]) was obtained.

(Sample 7)

Figure 18C:
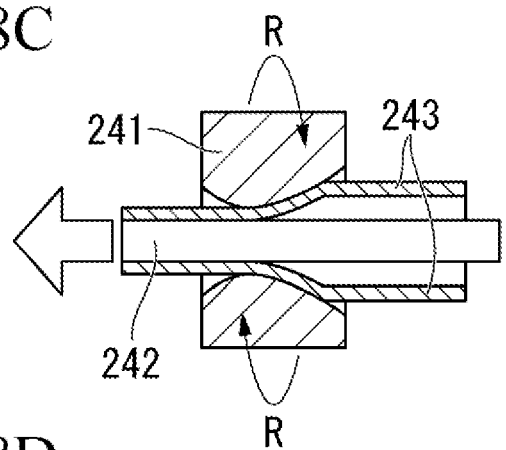
FIG. 18C is a view schematically showing a configuration of a rotating metal core drawing.

The Sample 7 was produced by using a "rotating metal core drawing" apparatus shown in FIG. 18C as the drawing method. In the apparatus of FIG. 18C, the part α of the die (first means) 101 includes means (not shown) for coming into contact with the outer surface of the round tube 103 which advances in the drawing direction D and rotating along the outer surface of the round tube.

More specifically, the apparatus of FIG. 18C is a drawing apparatus which includes at least first means 241 including a part α which surrounds a round tube 243 while being in contact therewith in the circumferential direction to reduce the diameter thereof, and cylindrical second means 242 which is disposed to oppose a minimum inner diameter portion of the part α and of which the side surface supports the round tube, in which the center axis of the minimum inner diameter portion and the center axis of the second means coincide with the drawing direction of the round tube, the first means and the second means are separated from each other over the entire circumferences thereof by a final thickness of the round tube, and the part α of the first means includes means (not shown) for coming into contact with the outer surface of the round tube which advances in the drawing direction and rotating along the outer surface of the round tube when the second means is allowed to advance in the drawing direction of the round tube according to the movement of the round tube while one end of the second means is allowed to protrude from the minimum inner diameter portion in the drawing direction of the round tube.

The drawing process was performed on the Sample 7 by inserting the long mandrel (of steel having a rigidity of 206 [GPa] and a tensile strength of 1900 [MPa]) which was not fixed, into the round tube which was processed to have an outer diameter of 1.92 [mm] and an inner diameter of 1.6 [mm] (a thickness of 160 [μm]) and was subjected to an annealing treatment at 400 [° C.] for 30 [min], inserting the round tube into the die along with the mandrel, and drawing out the round tube and the mandrel together in the atmosphere at room temperature while rotating the die. The processing was performed so that the reduction in the area of the cross-section of the round tube, which was perpendicular to the longitudinal direction, was 12.1 [%], and the thickness was 150 [μm] before and after the drawing process. The rotational speed of the die was 240 [rpm], and the drawing rate was 0.6 [mm/s]. The mandrel was removed after the drawing, and an annealing treatment was performed at 400 [° C.] for 30 [min]. By performing the above process, a long, thin, and narrow tube which was made of the AZ31 alloy and had an outer diameter of 1.8 [mm] and an inner diameter of 1.5 [mm] (a thickness of 150 [μm]) was obtained.

(Sample 8)

Figure 18D:
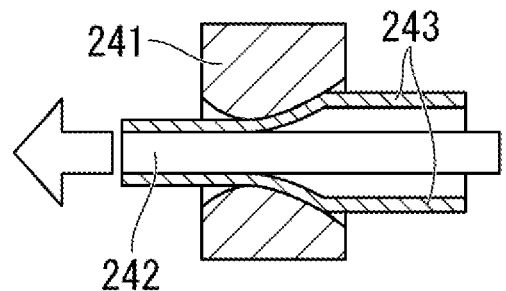
FIG. 18D is a view schematically showing a configuration of metal core drawing apparatus.

The Sample 8 was produced by using a "metal core (mandrel) drawing" apparatus shown in FIG. 18D as the drawing method. That is, the Sample 8 produced by the "metal core drawing" apparatus of the related art is a comparative example.

The apparatus of FIG. 18D differs from the above-described apparatus of FIG. 18C in that the part α of the first means does not include the means (not shown) for coming into contact with the outer surface of the round tube 103 which advances in the drawing direction and rotating along the outer surface of the round tube. The other features are the same as those of the above-described apparatus of FIG. 18C.

The Sample 8 is a comparative object of the above-described Samples 5 to 7, and the sample was produced by the metal core (mandrel) drawing apparatus of the related art. The drawing process was performed by inserting the long mandrel (of steel having a rigidity of 206 [GPa] and a tensile strength of 1900 [MPa]) which was not fixed, into the round tube which was processed to have an outer diameter of 1.92 [mm] and an inner diameter of 1.6 [mm] (a thickness of 160 [μm]) and was subjected to an annealing treatment at 400 [° C.] for 30 [min], inserting the round tube into the die along with the mandrel, and drawing out the round tube and the mandrel together in the atmosphere at room temperature. The processing was performed so that the reduction in the area of the cross-section of the round tube, which was perpendicular to the longitudinal direction, was 12.1 [%], and the thickness was 150 [μm] before and after the drawing process. The mandrel was removed after the drawing, and an annealing treatment was performed at 400 [° C.] for 30 [min]. By performing the above process, a long, thin, and narrow tube which was made of the AZ31 alloy and had an outer diameter of 1.8 [mm] and an inner diameter of 1.5 [mm] (a thickness of 150 [μm]) was obtained.

Figure 19A:
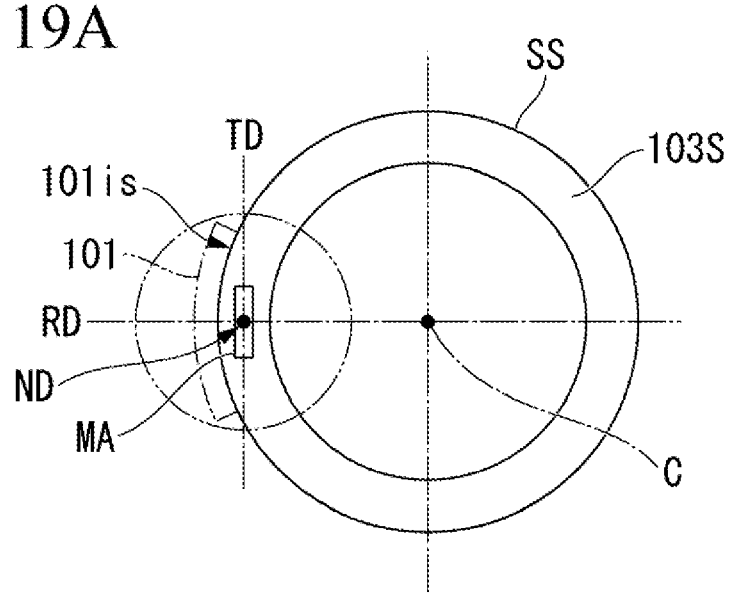
FIG. 19A is a schematic view showing the surface of a sample for EBSD measurement.
Figure 19B:
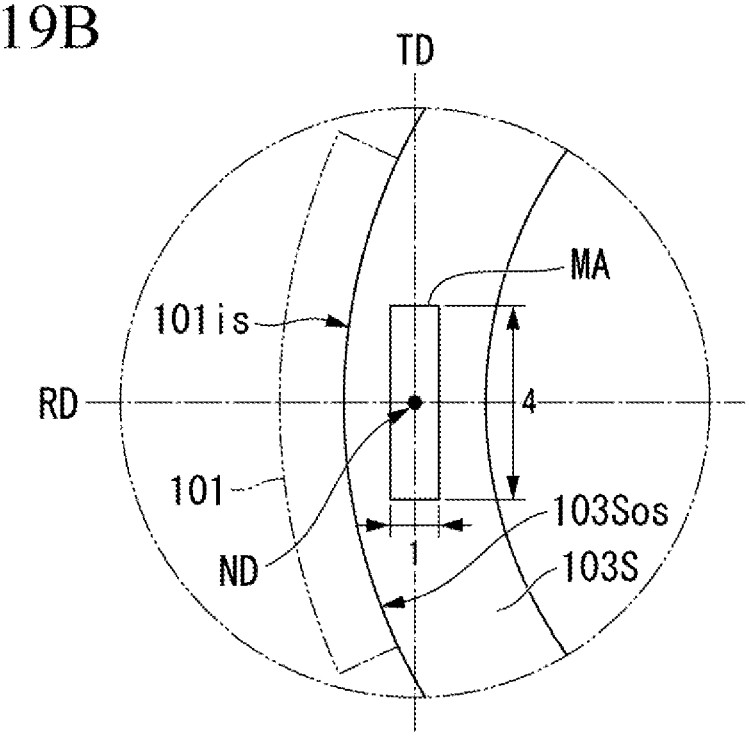
FIG. 19B is an enlarged plan view showing a partial region surrounded by a two-dot chain line in FIG. 19A.

(B) Evaluation of Crystal Structure by EBSD Method (B1) Production of Samples for EBSD Measurement The orientation of the basal plane (0001) of the crystal structure (hexagonal crystal structure) of each of the Samples 5 to 8 was measured by an electron back-scatter diffraction (EBSD) method. A sample SS for EBSD was produced in the following order. FIGS. 19A and 19B are schematic views showing the surface of the sample for EBSD measurement.

First, a sample S of the round tube was cut along a plane perpendicular to the axis (in the radial direction) by an electric discharge machine [FIG. 19A]. This was buried into a resin, and then the cut surface was polished by using emery papers in order of #400, #600, #800, #1000, #1500, and #2000 in this order. Next, the surface was mirror-finished by using alumina abrasive grains having a size of 1 micrometer. Thereafter, the finished surface of the sample was further polished by using an ion polishing device, thereby obtaining the sample SS for the EBSD measurement shown in FIGS. 19A and 19B. FIG. 19A is a plan view showing the entire surface of the finished sample SS, and FIG. 19B is an enlarged plan view showing a partial region surrounded by the two-dot chain line in FIG. 19A.

In addition, in FIGS. 19A and 19B, in order to illustrate the relative positional relationship between the die 101 and a round tube 103S which is a processed body, a part of the die 101 was shown by the two-dot chain line. The surface of the round tube 103S which is a processed body is denoted by 103Sos, and the inner surface of the die 101 which comes into contact with the surface 103Sos during the processing is denoted by 101*is*.

(B2) EBSD Measurement Method

A sample coordinate system for the EBSD measurement will be described with reference to FIGS. 19A and 19B.

As shown in FIGS. 19A and 19B, the EBSD measurement was performed on a range Ma in which a tube thickness center portion where the radial direction RD and the circumferential direction TD (a direction perpendicular to the radial direction RD) intersect with each other is the center in the radial cross-section (the figure perpendicular to the axis C of the round tube) and the aspect ratio of the height with respect to the width is 1:4. The measurement range MA in this measurement is about 100 μm×400 μm. The normal direction of the measurement surface during the EBSD measurement is an ND direction (a direction perpendicular to the figure) shown in FIGS. 20A to 20D. That is, ND is a viewpoint in the axial direction perpendicular to the radial cross-section.

(B3) EBSD Measurement Results

FIGS. 20A to 20D are graphs showing the EBSD measurement results regarding the Samples 5 to 8, respectively. More specifically, FIGS. 20A to 20D are graphs showing the orientations of the basal planes (0001) of the crystal structures (hexagonal crystal structures) of the Sample 5 to 8 in the RD (radial) direction and the TD direction (intersecting perpendicularly to the radial direction). FIGS. 20A to 20D respectively illustrate the EBSD measurement results of the Sample 5 (the fixed mandrel drawing), the Sample 6 (the rotating fixed-mandrel drawing), the Sample 7 (the rotating metal core drawing), and the Sample 8 (the metal core drawing). FIGS. 21A to 21D are image diagrams corresponding to FIGS. 20A to 20D, respectively, showing the orientations of the crystal structures (hexagonal crystal structures) regarding the Samples 5 to 8.

From the EBSD measurement results shown in FIGS. 20A to 20D, the following points became obvious.

(1) Sample 5 (Fixed Mandrel Drawing)

Figure 20A:
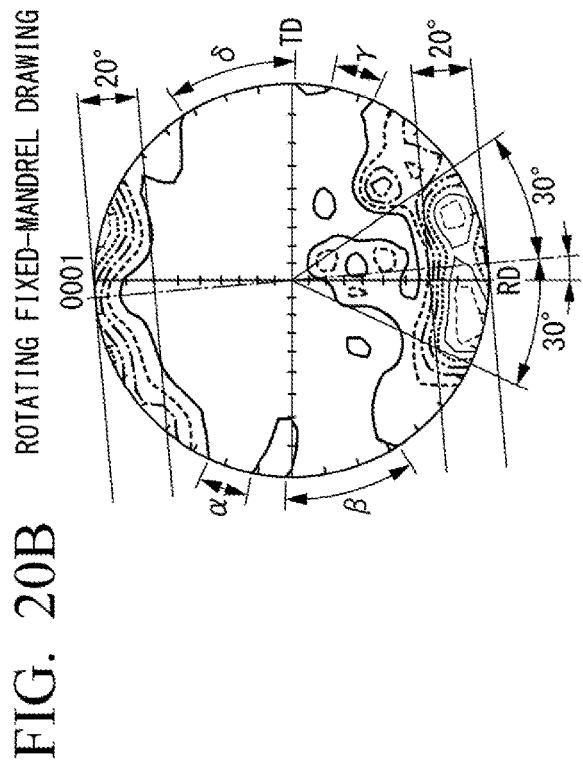
FIG. 20A is a graph showing the results of the EBSD measurement regarding Sample 5.

In FIG. 20A, the basal plane (0001) of the Sample 5 is inclined at 90° with respect to the circumferential direction, that is, is oriented along the circumferential direction. In 20A, a part on the TD right side is reflected because the measurement surface is inclined and is originally absent when the measurement surface has no inclination, that is, the distribution of (0001) is in a state of being vertically halved in the RD direction.

(2) Sample 6 (Rotating Fixed-Mandrel Drawing)

Figure 20B:
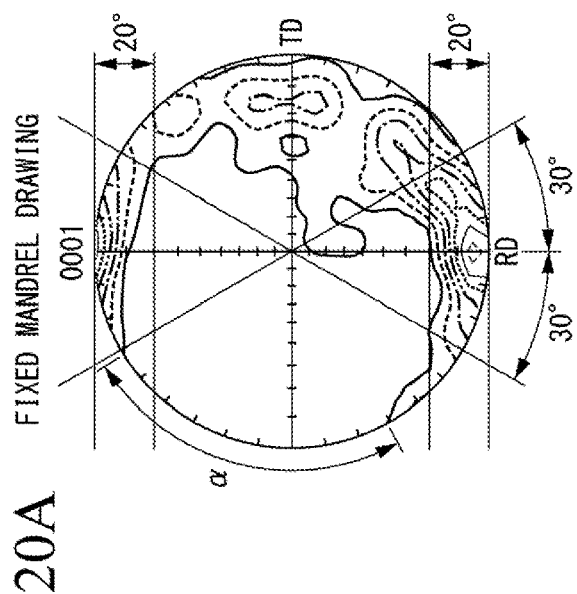
FIG. 20B is a graph showing the result of the EBSD measurement regarding Sample 6.
Figure 20C:
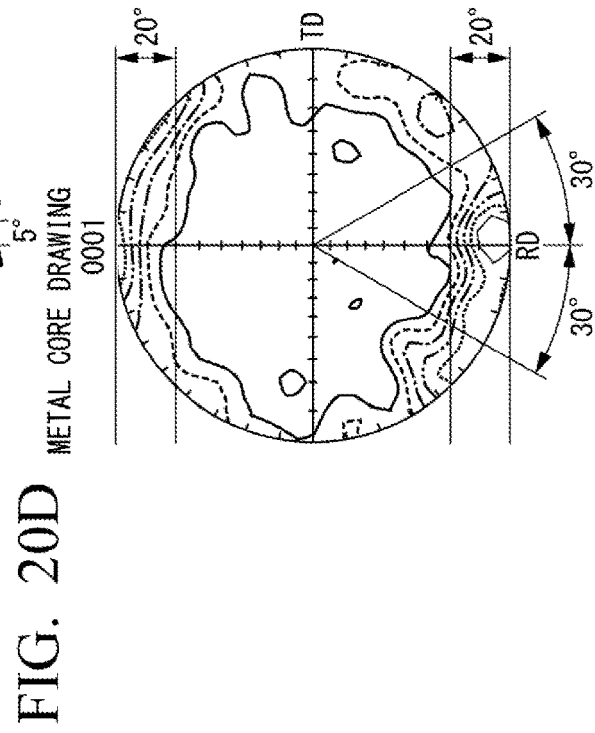
FIG. 20C is a graph showing the result of the EBSD measurement regarding Sample 7.

In FIG. 20B, the basal plane (0001) of the Sample 6 is oriented to be inclined at about 5° on average with respect to the circumferential direction.

(3) Sample 7 (Rotating Metal Core Drawing)

In 20C, the basal plane (0001) of the Sample 7 is oriented to be inclined at 65° on average with respect to the circumferential direction.

(4) Sample 8 (Metal Core Drawing)

Figure 20D:
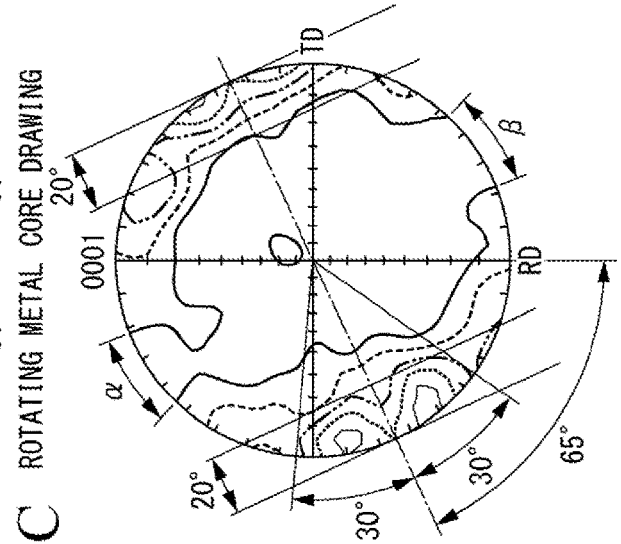
FIG. 20D is a graph showing the result of the EBSD measurement regarding Sample 8.
Figure 21A:
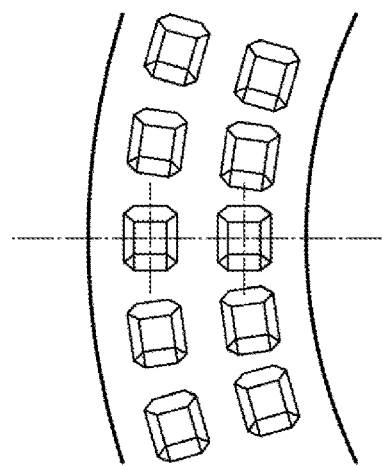
FIG. 21A is an image diagram showing the orientations of crystal structures (hexagonal crystal structures) regarding the Sample 5.
Figure 21B:
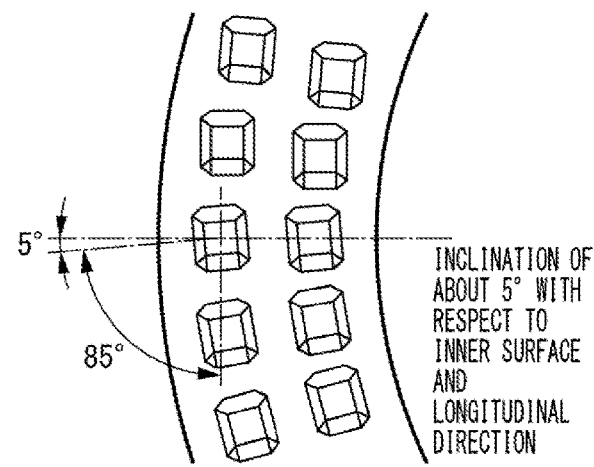
FIG. 21B is an image diagram showing the orientations of crystal structures (hexagonal crystal structures) regarding the Sample 6.
Figure 21C:
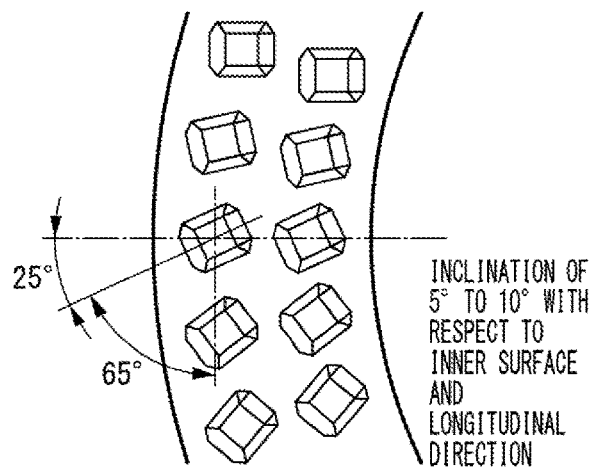
FIG. 21C is an image diagram showing the orientations of crystal structures (hexagonal crystal structures) regarding the Sample 7.
Figure 21D:
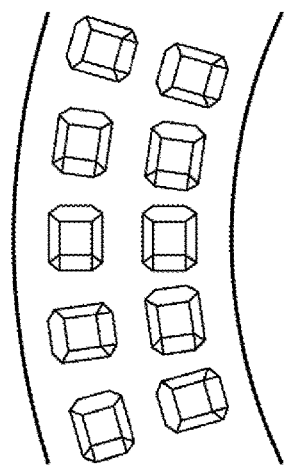
FIG. 21D is an image diagram showing the orientations of crystal structures (hexagonal crystal structures) regarding the Sample 8.

In FIG. 20D, the basal plane (0001) of the Sample 8 is randomly oriented in the circumferential direction and in the radial direction.

(5) The inclination angle of the basal plane (0001) in the circumferential direction depends on the rotational direction and speed of the die and the drawing rate. Therefore, the inclination angle is a factor which can be controlled by appropriately selecting the combination of the manufacturing conditions.

(6) In all the samples (Samples 5 to 8), a strong signal caused by a high-density orientation structure A having a peak intensity of 6/7 or more of the maximum peak intensity in the hexagonal basal plane (0001) is observed in a range of an inclination angle of ±30° with respect to the circumferential direction and an inclination angle of ±20° with respect to the round tube axis direction, and the high-density orientation structure A is oriented.

Particularly, in the round tube axis direction, both the upper half and the lower half of the pole figure need to be determined. An inclination of 20° means that the upper half is inclined downward from the front side and the lower half is inclined upward from the front side. Therefore, referring to FIGS. 20A to 20D, in all the samples (Samples 5 to 8), it is seen that the inclination angle with respect to the round tube axis direction is observed in a range of ±20°.

(7) The Samples 5 to 7 according to the present invention discretely include angle zones (α to δ) in which a weak signal caused by a low-density orientation structure B having a peak intensity of 1/7 of the maximum peak intensity in the hexagonal basal plane (0001) is observed. On the other hand, in the Sample 8 according to the manufacturing method of the related art, the weak signal caused by the low-density orientation structure B is continuously observed over the entire angle zones. Therefore, focusing on the weak signal caused by the low-density orientation structure B, the Samples 5 to 7 according to the present invention and the Sample 8 according to the manufacturing method of the related art can be distinguished from each other.

Figure 22A:
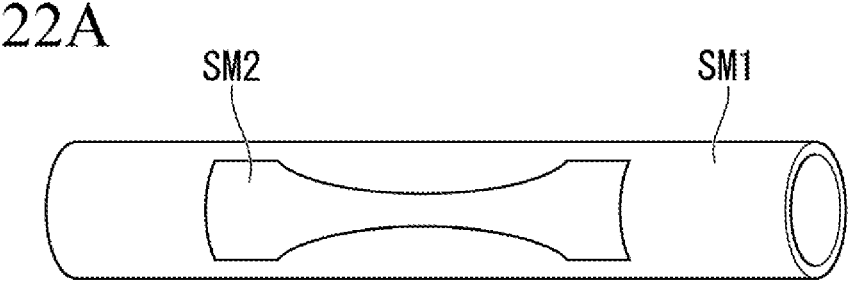
FIG. 22A is a schematic view showing a sample for measuring mechanical properties.
Figure 22B:
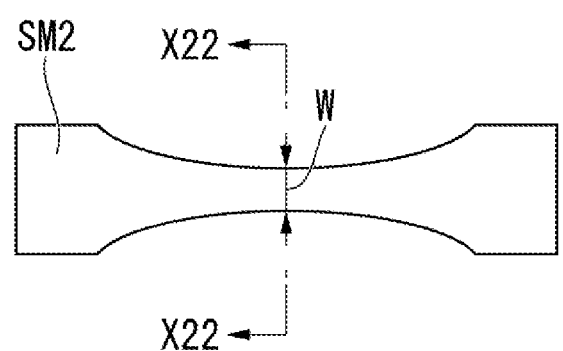
FIG. 22B is a schematic view showing a tensile test piece SM2 for measuring mechanical properties.
Figure 22C:
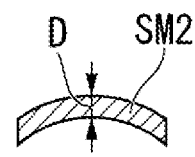
FIG. 22C is a cross-sectional view taken along X22-X22 of the tensile test piece SM2 shown in FIG. 22B.

(C) Evaluation of Mechanical Properties (C1) Production of Sample for Measuring Mechanical Properties FIGS. 22A to 22C are schematic views showing a sample for measuring mechanical properties. First, a sample SM1 was produced by cutting a thin, narrow tube (having an outer diameter of 1.8 mm and an inner diameter of 1.5 mm) made of an AZ31 alloy into a length of 70 mm [FIG. 22A]. Thereafter, a tensile test piece SM2 was cut out by performing an electric discharge process on the sample SM1 [FIG. 22B]. When the surface of the tensile test piece SM2 is viewed in a plan view, the width of the narrowest part is defined as a width W. FIG. 22C is a cross-sectional view taken along X22-X22 of the tensile test piece SM2 shown in FIG. 22B. In FIG. 22C, the thickness of the center portion of the tensile test piece SM2 is defined as a thickness D.

Here, in the shape of the tensile test piece SM2, a test piece shoulder portion R was 15 mm, a parallel portion width was 2 mm, a parallel portion length was 10 mm, a grip portion length was 10 mm, and the distance between marks was 7 mm.

(C2) Measurement Items of Mechanical Properties

A tensile test was performed by using the above-described tensile test piece SM2, and the tensile strength, the axial permanent elongation, the circumferential deformation ratio, and the thickness deformation ratio were evaluated.

The tensile test was performed under the conditions of 0.5 mm/min at room temperature until the test piece was broken. The tensile strength (0.2% Proof, UTS), the axial permanent elongation, the circumferential deformation ratio, and the thickness deformation ratio were respectively calculated by the following expressions.

Tensile strength [MPa]=maximum breaking strength [N]/test piece cross-sectional area [mm$^2$]

Axial permanent elongation [%]=(distance between marks before test−distance between marks after test)/distance between marks before test×100

Thickness deformation ratio [%]=(tube thickness before test−tube thickness after test)/tube thickness after test×100

Circumferential deformation ratio (also referred to as "width direction deformation ratio") [%]=(parallel portion width before test−parallel portion width after test)/parallel portion width before test×100

(C3) Measurement Results of Mechanical Properties

Table 1 shows the measurement results of the tensile strength (0.2% Proof, UTS), the axial permanent elongation, the circumferential deformation ratio, and the thickness deformation ratio for the above-described Samples 5 to 8.

TABLE 1

| Sample No. (manufacturing method) | Tensile strength [MPa] | | Deformation ratio [%] | | Crystal grain size [μm] |
|---|---|---|---|---|---|
| | 0.2% Proof | UTS | Elongation [%] | Thickness | Circumferential direction | |
| Sample 5 (fixed mandrel drawing) | 169 | 242 | 8.2 | 9.7 | 4.7 | 10.9 |
| Sample 6 (rotating fixed-mandrel drawing) | 167 | 244 | 10.2 | 7.6 | 4.3 | 16.8 |
| Sample 7 (rotating metal core drawing) | 169 | 244 | 8.9 | 7.5 | 7.5 | 9.1 |
| Sample 8: Related art (metal core (mandrel) drawing) | 168 | 247 | 10.0 | 6.8 | 4.0 | 14.2 |

From Table 1, the following points became obvious.

(1) Tensile strength: the dependence on the manufacturing method is rarely recognized.

(2) Axial permanent elongation: the axial permanent elongations of the present invention (Samples 5 to 7) can be controlled to be equal to or less than the same level as that in the related art (8 was used).

(3) Deformation ratio: the deformation ratios in both the thickness direction and the circumferential direction of the present invention (Samples 5 to 7) are higher than those in the related art (8 was used).

(4) Crystal grain size: the crystal grain sizes of the present invention (Samples 5 to 7) can be formed to be smaller than or larger than that in the related art (8 was used).

(5) The thickness deformation ratio of the Sample 5 is largest. The Sample 6 and the Sample 5 have the same tendency. The Sample 7 has high values in both the thickness deformation ratio and the high circumferential deformation ratio, and thus is most balanced.

(D) Immersion Test Using Artificial Body Fluid (D1) Production of Sample

In order to examine corrosion properties of the thin, narrow tube, that is, biodegradability in a living body, an immersion test was performed on the basis of the ASTM Standard G31-72.

A thin, narrow tube (an outer diameter of 1.8 mm and an inner diameter of 1.5 mm) made of an AZ31 alloy was cut into a length of 7 mm through electric discharge wire cutting, and thereafter the tube surface was polished by using an emery paper of #4000. The resultant was used as a sample for the immersion test. After measuring the weight of the sample by using an electronic balance, the sample was cleaned by acetone, 99.5% of anhydrous ethanol, and distilled water in this order as a pretreatment of the test.

Figure 23:
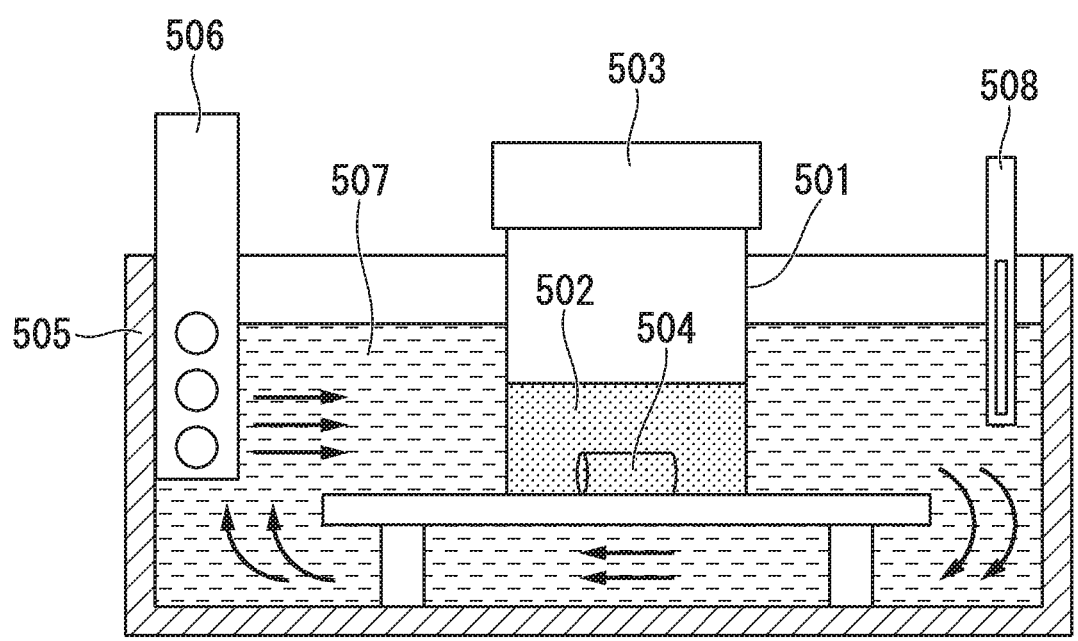
FIG. 23 is a schematic view showing an apparatus for an immersion test.

FIG. 23 is a schematic view showing an apparatus for the immersion test. In FIG. 23, 501 denotes a container, 502 denotes a simulated body fluid (SBF), 503 denotes a test container, 504 denotes a sample, 505 denotes a thermostatic bath, 506 denotes temperature control means, 507 denotes a liquid (water), and 508 denotes temperature measurement means.

(D2) Immersion Test

The immersion test was performed by preparing the test container 503 in which 50 ml of the simulated body fluid (SBF) 502 was put into the 250 ml container 501 subjected to a sterilization treatment and immersing the sample 504 in the simulated body fluid (SBF) 502 in the container 201. The test container 503 was disposed in the liquid (water) 507 which was circulated in the thermostatic bath 505 to meet the environment in the living body. The arrows shown in to in the liquid (water) 507 express the circulation. Accordingly, the simulated body fluid (SBF) 502 in the test container 503 was maintained at 37° C.

The sample 204 was removed after 18 hours from the start of the test, was cleaned by distilled water, and then was dried at room temperature. The weight of the dried sample 204 was measured by using an electronic balance, and a corrosion rate [mm/year] was calculated by the following expression.

Corrosion rate [mm/year]=(weight before test–weight after test)/sample surface area/immersion time×24×2.1

An example of the reference of the simulated body fluid (SBF) includes "How useful is SBF in predicting in vivo bone bioactivity?" by T. Kokubo et al., Biomaterials 27 (2006), pp. 2907-2915) 202.

(D3) Measurement Results of Immersion Test

Table 2 shows the measurement results of weight reduction, corrosion speed, and corrosion rate regarding the above-described Samples 5 to 8.

TABLE 2

| Sample No. (manufacturing method) | Weight reduction [%] | Corrosion speed [mg/cm$^2$/d] | Corrosion rate [%] |
|---|---|---|---|
| Sample 5 (fixed mandrel drawing) | 45.4 | 7.7 | 16.1 |
| Sample 6 (rotating fixed-mandrel drawing) | 33.2 | 5.3 | 11.2 |
| Sample 7 (rotating metal core drawing) | 11.3 | 1.7 | 3.6 |
| Sample 8: Related art (metal core (mandrel) drawing) | 7.1 | 1.1 | 2.4 |

From Table 2, the following points became obvious.

(1) Weight reduction: even though the material compositions of the thin, narrow tubes are the same (AZ31 alloy), the present invention (Samples 5 to 7) exhibited significantly higher weight reductions than that in the related art (8 was used). Only by adding rotation, the weight reduction is increased by 50% (the Sample 7 with respect to the Sample 8). The Sample 5 or the Sample 6 exhibited a weight reduction of about 4.5 to 6.5 times (the Samples 5 and 6 with respect to the Sample 8). The magnitude relationship between the weight reductions is "Sample 8<Sample 7<Sample 6<Sample 5".

(2) Corrosion speed: all of the present invention (Samples 5 to 7) exhibited significantly higher corrosion speeds than that in the related art (8 was used). This tendency is the same as that of the weight reduction, and the magnitude relationship between the corrosion speeds is also "Sample 8<Sample 7<Sample 6<Sample 5".

(3) Corrosion rate: all of the present invention (Samples 5 to 7) exhibited significantly higher corrosion rates than that in the related art (8 was used). This tendency is the same as that of the weight reduction, and the magnitude relationship between the corrosion rates is also "Sample 8<Sample 7<Sample 6<Sample 5".

When the above-described results are summarized, it was seen that the mechanical properties and the biodegradable properties of the thin, narrow tube according to the present invention are adjusted by controlling the processing method or the processing conditions without changing the composition of the Mg alloy. Therefore, the present invention significantly contributes to providing a thin, narrow tube for a biodegradable medical device.

INDUSTRIAL APPLICABILITY

The present invention relates to the manufacture of a long, thin, and narrow tube made of magnesium or a magnesium alloy, which can be mainly used as a member for a minimally-invasive stent that melts away in vivo in a medical technology field and can also be used as an implant member or an artificial bone member.

REFERENCE SIGNS LIST

100, 120 drawing apparatus
101, 211, 221, 231, 241 die (first means)
102, 122, 212, 222, 232, 242 mandrel (second means)
102a, 122a one end
102 C, 105 C, 122 C, 125 C center axis
102d side surface
103a, 123a, 213a, 223a, 233a, 243a inner wall surface
104, 124 fixing tool
105, 125 through-hole
105A, 125A minimum inner diameter portion
105B, 125B, 105D, 125D opening
121 roll
121a groove
222A support bar
222B, 232 plug
D drawing direction
R1 final outer diameter
R2 final inner diameter
R3 outer diameter
R4 inner diameter
dR thickness
α part

The invention claimed is:

1. A drawing system for manufacturing a component of a biodegradable medical device, the system comprising: a round tube made of a magnesium alloy (Mg) having a hexagonal crystal structure, and the magnesium alloy forming the round tube, viewed in a round tube axis direction of the round tube, has hexagonal basal planes (0001) of crystals of magnesium alloy oriented at a predetermined inclination angle with respect to a circumferential direction perpendicular to a radial direction of the round tube, and a drawing apparatus comprising at least:
first means including a part (α) which surrounds the round tube while being in contact with the round tube in a circumferential direction to reduce a diameter of the round tube; and
cylindrical second means which is disposed to oppose a minimum inner diameter portion of the part (α) and of which a side surface supports the round tube,
wherein a center axis of the minimum inner diameter portion and a center axis of the second means coincide with a drawing direction of the round tube, and
the first means and the second means are separated from each other over entire circumferences by a thickness of the round tube,
wherein the second means protrudes from the minimum inner diameter portion in the drawing direction of the round tube and permits the round tube to slide thereon as the drawing proceeds, and the round tube and the second means are configured to be separated from each other by sliding on each other,
wherein the first means comprises a die or rolls, and
wherein the second means is a mandrel.

2. The system according to claim 1, wherein the part (α) of the first means comes into contact with an outer surface of the round tube which advances in the drawing direction and is rotatable and rotates along the outer surface of the round tube.

3. A system for manufacturing a component of a biodegradable medical device, the system comprising: a round tube made of a magnesium alloy (Mg) having a hexagonal crystal structure, and the magnesium alloy forming the round tube, viewed in a round tube axis direction of the round tube, has hexagonal basal planes (0001) of crystals of magnesium alloy oriented at a predetermined inclination angle with respect to a circumferential direction perpendicular to a radial direction of the round tube, an apparatus comprising at least:
first means including a part (α) which surrounds the round tube while being in contact with the round tube in a circumferential direction to reduce a diameter of the round tube; and
cylindrical second means which is disposed to oppose a minimum inner diameter portion of the part (α) and of which a side surface supports the round tube,
wherein a center axis of the minimum inner diameter portion and a center axis of the second means coincide with a drawing direction of the round tube,
the first means and the second means are separated from each other over entire circumferences by a final thickness of the round tube,
the part (α) of the first means comes into contact with an outer surface of the round tube which advances in the drawing direction and is rotatable and rotates along the outer surface of the round tube when the second means advances in the drawing direction of the round tube according to movement of the round tube while one end of the second means protrudes from the minimum inner diameter portion in the drawing direction of the round tube, and permits the round tube to slide thereon as the drawing proceeds, and the round tube and the second means are configured to be separated from each other by sliding on each other,
wherein the first means comprises a die or rolls, and
wherein the second means is a mandrel.

4. The system according to claim 1, wherein one end of the second means protrudes outward from a space surrounded by the first means.

5. A manufacturing method for a tube of a biodegradable medical device, using a drawing apparatus,
said tube comprising a round tube made of a magnesium alloy (Mg) having a hexagonal crystal structure, and
the magnesium alloy forming the round tube, viewed in a round tube axis direction of the round tube, has hexagonal basal planes (0001) of crystals of magnesium alloy oriented at a predetermined inclination angle with respect to a circumferential direction perpendicular to a radial direction of the round tube,
the drawing apparatus comprising at least:
first means including a part ($\alpha$) which surrounds the round tube while being in contact with the round tube in a circumferential direction to reduce a diameter of the round tube; and
cylindrical second means which is disposed to oppose a minimum inner diameter portion of the part ($\alpha$) and of which a side surface supports the round tube,
wherein a center axis of the minimum inner diameter portion and a center axis of the second means coincide with a drawing direction of the round tube, and
the first means and the second means are separated from each other over entire circumferences by a thickness of the round tube, and the method comprising:
protruding the second means from the minimum inner diameter portion in the drawing direction of the round tube and retreating the second means opposite the drawing direction while moving the round tube in the drawing direction.

6. The manufacturing method according to claim 5,
wherein the part ($\alpha$) of the first means comes into contact with an outer surface of the round tube which advances in the drawing direction and further comprising rotating the first means along the outer surface of the round tube.

7. The manufacturing method according to claim 5, wherein one end of the second means protrudes outward from a space surrounded by the first means.

8. The manufacturing method according to claim 5, wherein the first means is a die.

9. The manufacturing method according to claim 5, wherein the first means comprises rolls.

10. The manufacturing method according to claim 5, wherein the second means is a mandrel.

11. A manufacturing method for a tube of a biodegradable medical device, using a drawing apparatus, said tube comprising a round tube made of a magnesium alloy (Mg) having a hexagonal crystal structure, and
the magnesium alloy forming the round tube, viewed in a round tube axis direction of the round tube, has hexagonal basal planes (0001) of crystals of magnesium alloy oriented at a predetermined inclination angle with respect to a circumferential direction perpendicular to a radial direction of the round tube,
the apparatus comprising at least:
first means including a part ($\alpha$) which surrounds the round tube while being in contact with the round tube in a circumferential direction to reduce a diameter of the round tube; and
cylindrical second means which is disposed to oppose a minimum inner diameter portion of the part ($\alpha$) and of which a side surface supports the round tube,
wherein a center axis of the minimum inner diameter portion and a center axis of the second means coincide with a drawing direction of the round tube, the first means and the second means are separated from each other over entire circumferences by a final thickness of the round tube, and the method comprising:
putting the part ($\alpha$) of the first means into contact with an outer surface of the round tube;
advancing the round tube in the drawing direction; and
rotating the first means along the outer surface of the round tube while the second means extends beyond the minimum inner diameter portion of the part ($\alpha$) in the drawing direction of the round tube.

* * * * *